(12) United States Patent
Cheetham et al.

(10) Patent No.: US 11,771,119 B2
(45) Date of Patent: Oct. 3, 2023

(54) METHOD OF MAKING A FLAVOURED SWEETENER AND USES THEREOF

(71) Applicant: COCONUTZ PTE. LTD., Singapore (SG)

(72) Inventors: Peter Samuel James Cheetham, Warwichshire (GB); Christoph Langwallner, Singapore (SG); Margit Langwallner, Singapore (SG); Christian Hermansen, Singapore (SG); Candy Chuing Tey Shiang, Singapore (SG); Wen Jue Amelia Tan, Singapore (SG)

(73) Assignee: COCONUTZ PTE. LTD., Singapore (SG)

( * ) Notice: Subject to any disclaimer, the term of this patent is extended or adjusted under 35 U.S.C. 154(b) by 66 days.

(21) Appl. No.: 16/315,384

(22) PCT Filed: Jul. 5, 2017

(86) PCT No.: PCT/SG2017/050343
§ 371 (c)(1),
(2) Date: Jan. 4, 2019

(87) PCT Pub. No.: WO2018/009149
PCT Pub. Date: Jan. 11, 2018

(65) Prior Publication Data
US 2019/0297930 A1    Oct. 3, 2019

(30) Foreign Application Priority Data
Jul. 5, 2016  (SG) .................. 10201605526W

(51) Int. Cl.
*A23L 27/30*    (2016.01)
*A23L 5/00*    (2016.01)
(Continued)

(52) U.S. Cl.
CPC .................. *A23L 27/33* (2016.08); *A23L 5/15* (2016.08); *A23L 5/51* (2016.08); *A23L 19/10* (2016.08);
(Continued)

(58) Field of Classification Search
CPC . A23L 5/51; A23L 19/10; A23L 23/00; A23L 27/33; A23L 27/24; A23L 29/30;
(Continued)

(56) References Cited

U.S. PATENT DOCUMENTS 2,880,094 A * 3/1959 Naghski .................. C13B 50/00
426/48
9,161,562 B2   10/2015 Kannar et al.
2019/0071739 A1   3/2019 Rowe

FOREIGN PATENT DOCUMENTS

JP   2008501321   1/2008
JP   2015534455   12/2015
KR   100742174 B1   7/2007

OTHER PUBLICATIONS

Godshall, MA Chapter 15 Flavor and Odor in Sugarcane Products In Chemistry and Processing of Sugarbeet and Sugarcane, edited by M.A. Clarke and M.A. Godshall Elsevier Science Publishers B.V., Amsterdam, 1988. (Year: 1988).*

(Continued)

*Primary Examiner* — Subbalakshmi Prakash
(74) *Attorney, Agent, or Firm* — Troutman Pepper Hamilton Sanders LLP

(57) ABSTRACT

A method of making a flavoured sweetener or food product by incubating an unrefined plant extract containing sucrose as the main solute with a microorganism or microorganisms to form a modified unrefined plant extract; evaporating water from the modified sucrose-based plant extract to form a concentrate; and cooking the concentrate to develop colour and flavour to produce the flavoured sweetener is disclosed.

(Continued)

The flavoured sweetener can serve as a coconut sugar substitute. In a preferred embodiment the unrefined plant extract comprises sugarcane juice or sugar beet juice, and the microorganisms may be selected from *Stenotrophomonas maltophilia, Bacillus subtilis, Bacillus flexus*, or a *Klyveromyces* species. The flavoured sweetener can be used to make a range of food and beverage ingredients and also food products including sauces, natural flavour extracts and flavour molecules, chocolate, health foods and convenience forms of the various forms of flavoured sweeteners.

13 Claims, 4 Drawing Sheets

(51) Int. Cl.

| | | |
|---|---|---|
| *A23L 27/24* | (2016.01) | |
| *A23L 23/00* | (2016.01) | |
| *A23L 27/50* | (2016.01) | |
| *A23L 5/10* | (2016.01) | |
| *A23L 19/10* | (2016.01) | |
| *C13B 20/00* | (2011.01) | |
| *C13B 30/00* | (2011.01) | |
| *C13B 10/02* | (2011.01) | |
| *A23L 29/30* | (2016.01) | |
| *C13K 1/02* | (2006.01) | |
| *C13B 50/00* | (2011.01) | |
| *C12N 1/00* | (2006.01) | |
| *C12N 1/14* | (2006.01) | |
| *C12N 1/20* | (2006.01) | |
| *C12R 1/00* | (2006.01) | |
| *C12R 1/125* | (2006.01) | |
| *C12R 1/645* | (2006.01) | |

(52) U.S. Cl.
CPC ............... *A23L 23/00* (2016.08); *A23L 27/24* (2016.08); *A23L 27/30* (2016.08); *A23L 27/50* (2016.08); *A23L 29/30* (2016.08); *A23L 29/35* (2016.08); *C13B 10/02* (2013.01); *C13B 20/002* (2013.01); *C13B 30/002* (2013.01); *C13B 50/002* (2013.01); *C13K 1/02* (2013.01); *A23V 2002/00* (2013.01); *C12N 1/00* (2013.01); *C12N 1/145* (2021.05); *C12N 1/205* (2021.05); *C12R 2001/00* (2021.05); *C12R 2001/125* (2021.05); *C12R 2001/645* (2021.05)

(58) Field of Classification Search
CPC . A23L 27/50; A23L 5/15; A23L 29/35; A23L 27/30; C13B 20/002; C13B 50/002; C13B 30/002; C13B 10/02; C13K 1/02; C12R 1/00; C12R 1/125; C12R 1/645; A23V 2002/00
USPC .......................................................... 426/48
See application file for complete search history.

(56) References Cited

OTHER PUBLICATIONS

Martinez et al. Journal of cleaner production 2017 v.158 pp. 8-17, abstract (Year: 2017).*
De Araujo et al. Applied Biochemistry and Biotechnology vols. 98-100, 2002, 774 abstract (Year: 2002).*
Communication (International Preliminary Report of Patentability) for International Application No. PCT/SG2017/050343, dated Jun. 11, 2018, 10 pages total.
Communication (International Search Report) for International Application No. PCT/SG2017/050343, dated Sep. 25, 2017, 6 pages total.
Communication (Written Opinion) for International Application No. PCT/SG2017/050343, dated Sep. 20, 2017, 6 pages total.
Chen, P. et al . . . , "A Microbial Transformation Using Bacillus Subtilis B7-S to Produce Natural Vanillin from Ferulic Acid" Scientific Reports (2016) vol. 6, No. 20400, pp. 1-10.
Hall, H.H. et al., "Microörganisms Causing Fermentation Flavors in Cane Sirups, Especially Barbados 'Molasses'" Journal of Bacteriology (1937) vol. 33, No. 6, pp. 577-585.
Axe, J. "5 Best Sugar Substitutes" 9 pages total, https://draxe.com/sugar-substitutes/.
Allrecipes Dish, "Here's How To Make Caramel Sauce" 12 pages total, https://web.archive.org/web/20160620020450/http://dish.allrecipes.com/heres-how-to-make-caramel-sauce.
Beckett ST, "Chocolate ingredients," Science of Chocolate, Royal Society of Chemistry (2000) p. 8-30, XP002347896.
Database GNPD[Online] MINTEL, "Soy Sauce with Toasted Sesame Seeds," (2015) XP055661614, retrieved from www.gnpd.com Database accession No. 3120893.
Communication (Extended European Search Report) received in European Application No. 17824649.2 dated Feb. 6, 2020, 11 pages total.
Roling, W.F.M. et al., "Changes in microflora and biochemical composition during the Baceman stage of traditional Indonesian Kecap (soy sauce) production," Journal of Fermentation and Bioengineerin (1994) vol. 77, No. 1, p. 62-70.
Steinhaus, P. et al., "Characterization of the Key Aroma Compounds in Soy Sauce Using Approaches of Molecular Sensory Science," Journal of Agricultural and Food Chemistry (2007) vol. 55, No. 15, p. 6262-6269, . XP055081976, ISSN: 0021-8561, DOI: 10.1021/jf0709092.

* cited by examiner

METHOD OF MAKING A FLAVOURED SWEETENER AND USES THEREOF

CROSS-REFERENCE TO RELATED APPLICATIONS

This application is a U.S. National Phase application under 35 U.S.C. § 371 of International Patent Application No. PCT/SG2017/050343, filed on Jul. 5, 2017, which claims priority to Singapore Patent Application No. SG 10201605526W, filed on Jul. 5, 2016, all of which applications are incorporated herein by reference in their entireties.

FIELD

The invention relates to flavoured sweeteners and methods of making and using flavoured sweeteners.

BACKGROUND

Coconut sugar (CNS) is a traditional Southeast-Asian flavoured sweetener produced on small scales by very large numbers of individual farmers in countries such as Malaysia, Indonesia, Philippines and India, collectively with overall sales of well over $2B. CNS is technically a 'by-product' of the coconut tree, where the inflorescences of the tree are partially tapped for their sap, which is then made by evaporative heating over open fires, whereas coconut trees are typically grown for their fruit (for reproduction, coconut water, coconut flesh, coconut oil, coconut milk or other products derived from coconut husks/shells). The incision of the flower cluster often prevents the coconut plant from reproducing thus often not resulting in a fruit.

Various forms of CNS are produced all over Southeast Asia, which differ especially in their flavours, so that some forms are preferred to others especially pertaining to native cultures and taste preferences. While each of these sugars are characteristically CNSs, having been made from the same or similar process and coconut saps, they possess flavour nuances and so are distinct from each other. Industrially, it has been known that only certain types of CNSs from particular regions are preferred ingredients for additional processing into sweet sauce.

CNS has a subtle, complex flavour, and its flavour is used in a range of food and beverages, particularly as the key ingredient of Southeast-Asian sauces and sweet sauce. Sweet sauce contains up to 80 wt. % CNS, the rest being mostly soy sauce and spices. There is a marked increase in demand for sweet sauce in Southeast Asia, and for CNS as a healthy food substitute for many western consumers. However for some time CNS has been in short supply due to the limited number of coconut palm trees, the relatively low production of CNS per hectare, weakening of the trees by continually being tapped for their sap, the many years new trees take to grow before they can become productive, labour shortage on farms, seasonal availability of coconut sap due to climate and various weather conditions, the short shelf life of sap reducing any possibility of centralised operations, and the physical dangers farmers face twice daily when climbing the trees to tap their flower buds to collect the coconut sap. No centralised process is possible that can ensure higher quality control. Add to this the demand for other coconut products made from the fruit and there is a need for alternative flavoured sweeteners and alternative means of making flavoured sweeteners and products that can be made by the flavoured sweeteners such as sweet sauce.

Due to the shortage of CNS, the industry now supplements CNS with jaggery, molasses and various forms of sugarcane sugar as fillers in the production of sweet sauce, which results in a less than ideal flavour quality of the final product, and increased complexity required in blending of the various sugars together to achieve consistently standardised organoleptic profiles in the final sweet sauce product produced for consumers.

Because of its popularity in its own right and effects from urbanisation, and for use as the key ingredient for sweet sauce, demands for CNS have risen steadily. In addition to the variabilities in the supply of CNS inherent in its production by so many small farmers an additional problem in using CNS is that because of this multitude of individual farmers there are very wide variations in the quality characteristics of the individual supplies of CNSs. Consequentially the manufacturers of the consumer products that use CNS as a key ingredient have to carry out complex blending operations so as to ensure a consistent quality of the CNS they use as an ingredient, in order to meet the flavour and other quality standards of their branded products. In addition, many producers add undesirable preservatives such as sulphite as an antimicrobial preservative and stabiliser, thus detracting from the healthiness of the sweet sauce made from CNSs. In addition, three undesirable features of CNSs as currently produced are that the coconut sap is often contaminated by insects and other creatures, residues of which become part of the CNS, ash and smoke from the open fires used to concentrate the sap also contaminate the CNS, and in addition the flavour of the CNS is unstable, changing in character with time. Due to the method of collection of the coconut sap the process of making CNS is not industrially scalable.

Consequentially there is a need for alternative flavoured sweeteners and alternative means of making flavoured sweeteners to ameliorate at least one of the problems mentioned above.

SUMMARY

It is an object of the present invention to provide an improved flavoured sweetener, and/or means of making the same and/or the use of the flavoured sweetener in producing food products and/or food products containing the flavoured sweetener.

Accordingly, an aspect of the invention provides a process for making a flavoured sweetener comprising: (a) incubating an unrefined plant extract containing sucrose as the main solute with a microorganism or microorganisms to form a modified unrefined plant extract; and (b) heating the modified unrefined plant extract to produce the flavoured sweetener.

Another aspect of the invention provides a modified unrefined plant extract derivable by the method comprising, incubating an unrefined plant extract containing sucrose as the main solute with a microorganism or microorganisms to form a modified unrefined plant extract.

Another aspect of the invention provides a flavoured sweetener derivable by the process disclosed herein, further comprising: a first characteristic comprising at least one selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 5 or greater; and (E)-1-(2,6,6-trimethyl-1-cyclohexa-1,3-dienyl)but-2-en-1-one present at a flavour dilution number of at least 8; a second characteristic comprising at least one selected from glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %; and; a third characteristic comprising at least one selected from the group comprising: 3-Hydroxy-4,5-dimethyl-2(5H)-furanone at a flavour dilution number of at least 10, 4-Hydroxy-3-methoxybenzaldehyde at a flavour dilution number of at least 7, 4-Hydroxy-2,5-dimethyl-3(2H)-furanone at a flavour dilution number of at least 5, 3-Methylsulfanylpropanal, Acetic acid, 2-Methylbutanoic acid/3-methylbutanoic acid, 2-Phenylpropionic acid/3-Phenylpropionic acid, Phenylacetic acid, 2-Methoxy-4-prop-1-en-2-ylphenol, (E)-1-(2,6,6-trimethyl-1-cyclohexa-1,3-dienyl)but-2-en-1-one, 2-Methylbutanal/3-Methylbutanal, (E)-3-[(2S,3R)-3-Pentyl oxiran-2-yl]prop-2-enal, 2-methoxy-4-prop-2-enylphenol, and 2-Methoxyphenol.

Another aspect of the invention provides a flavour extract derivable by the process as described herein comprising at least ten of the flavour molecules selected from the group comprising: 3-Hydroxy-4,5-dimethyl-2(5H)-furanone; 4-Hydroxy-3-methoxybenzaldehyde; 4-Hydroxy-2,5-dimethyl-3(2H)-furanone; 3-Methylsulfanylpropanal; Acetic acid; 2-Methylbutanoic acid/3-methylbutanoic acid; 2-Phenylpropionic acid/3-Phenylpropionic acid; Phenylacetic acid; 2-Methoxy-4-prop-1-en-2-ylphenol; (E)-1-(2,6,6-Trimethyl-1-cyclohexa-1,3-dienyl)but-2-en-1-on; 2-Methylbutanal/3-Methylbutanal; (E)-3-[(2S,3R)-3-Pentyloxiran-2-yl]prop-2-enal; 2-Methoxy-4-prop-2-enylphenol; or 2-methoxyphenol; or a combination thereof.

Another aspect of the invention provides a process or method for manufacturing a food product, comprising: (a) incubating an unrefined plant extract containing sucrose as the main solute with a microorganism or microorganisms to form a modified unrefined plant extract; (b) heating the modified unrefined plant extract to produce a flavoured sweetener; (c) mixing the flavoured sweetener with an additional ingredient; and (d) forming the food product.

Another aspect of the invention provides a food product derivable by the process or method for manufacturing a food product as described herein comprising: a first characteristic comprising at least one selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 5 or greater; and (E)-1-(2,6,6-trimethyl-1-cyclohexa-1,3-dienyl)but-2-en-1-one present at a flavour dilution number of at least 8; a second characteristic comprising at least one selected from glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %; and; a third characteristic comprising at least one selected from the group comprising: 3-Hydroxy-4,5-dimethyl-2(5H)-furanone at a flavour dilution number of at least 10, 4-Hydroxy-3-methoxybenzaldehyde at a flavour dilution number of at least 7, 4-Hydroxy-2,5-dimethyl-3(2H)-furanone at a flavour dilution number of at least 5, 3-Methylsulfanylpropanal, Acetic acid, 2-Methylbutanoic acid/3-methylbutanoic acid, 2-Phenylpropionic acid/3-Phenylpropionic acid, Phenylacetic acid, 2-Methoxy-4-prop-1-en-2-ylphenol, (E)-1-(2,6,6-trimethyl-1-cyclohexa-1,3-dienyl)but-2-en-1-one, 2-Methylbutanal/3-Methylbutanal, (E)-3-[(2S,3R)-3-Pentyl oxiran-2-yl]prop-2-enal, 2-methoxy-4-prop-2-enylphenol, and 2-Methoxyphenol wherein the first, second and third characteristics are proportional to the flavoured sweetener content of the food product.

Another aspect of the invention provides a sweet sauce derivable by the process or method for manufacturing a food product as described herein, the sweet sauce comprising a first characteristic comprising at least one selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 0.5 or greater; and (E)-1-(2,6,6-trimethyl-1-cyclohexa-1,3-dienyl)but-2-en-1-one present at a flavour dilution number of at least 8; a second characteristic comprising at least one selected from glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %; and; a third characteristic comprising at least one selected from the group comprising: 3-Hydroxy-4,5-dimethyl-2(5H)-furanone at a flavour dilution number of at least 10, 4-Hydroxy-3-methoxybenzaldehyde at a flavour dilution number of at least 7, 4-Hydroxy-2,5-dimethyl-3(2H)-furanone at a flavour dilution number of at least 5, 3-Methylsulfanylpropanal, Acetic acid, 2-Methylbutanoic acid/3-methylbutanoic acid, 2-Phenylpropionic acid/3-Phenylpropionic acid, Phenylacetic acid, 2-Methoxy-4-prop-1-en-2-ylphenol, (E)-1-(2,6,6-trimethyl-1-cyclohexa-1,3-dienyl)but-2-en-1-one, 2-Methylbutanal/3-Methylbutanal, (E)-3-[(2S,3R)-3-Pentyl oxiran-2-yl]prop-2-enal, 2-methoxy-4-prop-2-enylphenol, and 2-Methoxyphenol wherein the first, second and third characteristics are proportional to the flavoured sweetener content of the sweet sauce.

Another aspect of the invention provides a process of reducing the sucrose content in a flavoured sweetener comprising affination, filtration, centrifugation or solvent extraction.

Other aspects of the invention will become apparent to those of ordinary skill in the art upon review of the following description of specific embodiments of the invention in conjunction with the accompanying figures.

BRIEF DESCRIPTION OF THE DRAWINGS

The present invention will now be described, by way of illustrative example only, with reference to the accompanying drawings, of which.

DETAILED DESCRIPTION

Figure 1:
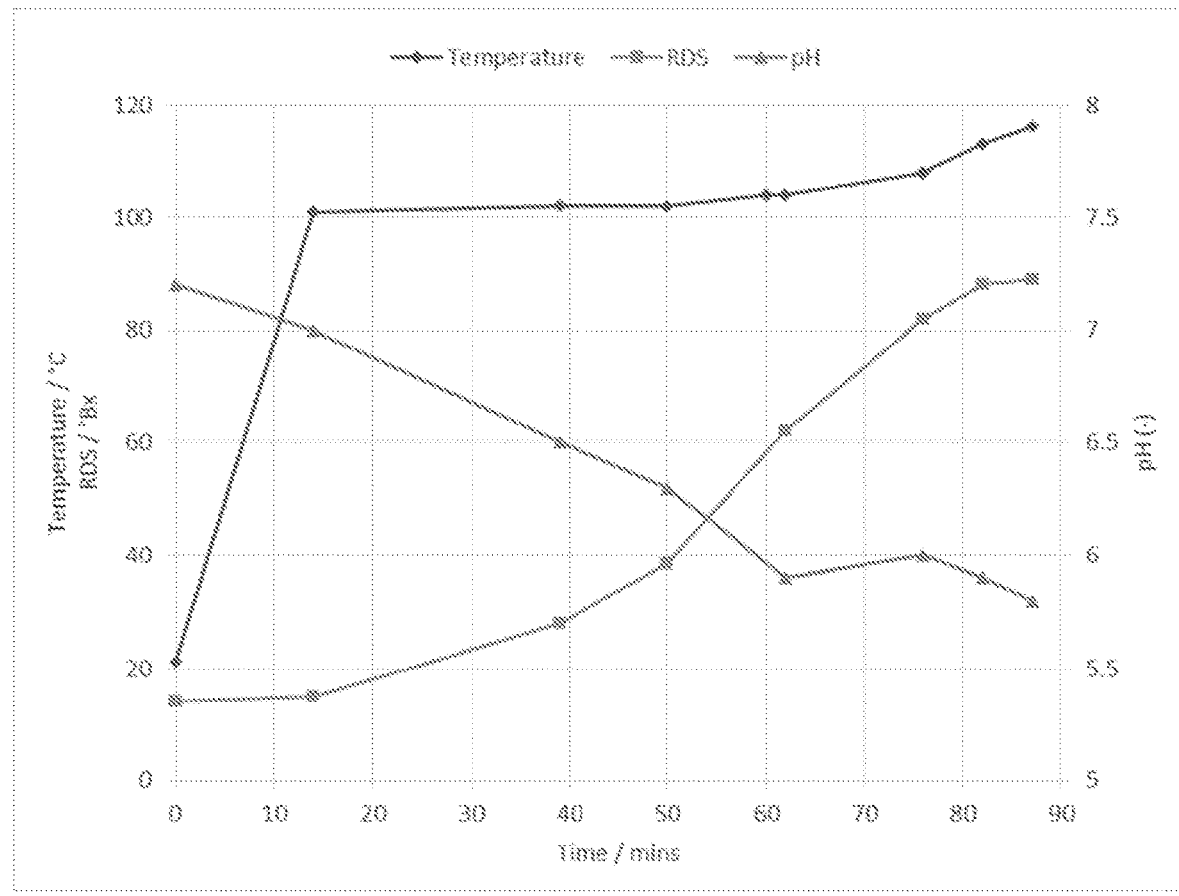
FIG. 1. Time profile for evaporation and cooking of the incubated sugarcane juice monitoring Refractometric Dry substances (RDS) content, pH and temperature. The initial volume of incubated sugarcane juice is 1 kg and the evaporator effect is around 800 W.

In response to these combined supply and demand problems a new and scalable process has been developed to make new types of flavoured sweeteners to substitute CNS; which have all of the individual flavour characteristics, texture, colour and other characteristics of the traditional product, as assessed as a product in its own right and as an ingredient in applications such as in sweet sauce by extensive instrumental and taste panel analysis.

Accordingly, an aspect of the invention provides a process for making a flavoured sweetener comprising: (a) incubating an unrefined plant extract containing sucrose as the main solute with a microorganism or microorganisms to form a modified unrefined plant extract; and (b) heating the modified unrefined plant extract to produce the flavoured sweetener.

As used herein the term 'unrefined plant extract containing sucrose as the main solute' refers to a composition of a minimally processed plant extract comprising sucrose as the main solute by wt % of the extract, extracted from a plant. In various embodiments the unrefined plant extract solutes may comprise less than 50% sucrose but the predominant component of the plant extract solutes on a wt % is sucrose. In various embodiments the unrefined plant extract may be obtained by collection of sap from a plant, mechanical crushing or any other means known in the art for obtaining sugar solutions directly from plants. In an example, the unrefined plant extract containing sucrose as the main solute includes sugar beet juice.

As used herein the term 'incubation' refers culturing a microorganism or microorganisms in the unrefined plant extract containing sucrose as the main solute whereby a metabolic process is initiated. The metabolic process may include catabolism, anabolism or fermentation.

As used herein the term 'flavoured sweetener' refers to any composition comprising predominantly monosaccharides or disaccharides or a combination of monosaccharides and disaccharides further comprising natural flavour molecules as described herein. This will provide the advantage of producing flavoured sweeteners to substitute coconut sugar; with all of the individual flavour characteristics, mouth feel, colour, comparable glycaemic index (GI), and other characteristics of the traditional product via a cheaper and simpler process. The term 'flavoured sweetener' also refers to any composition that provides a 'flavourant' defined as a substance that gives another substance flavour which may alter the characteristics of a solute causing it to become sweet, sour, tangy, etc.

In various embodiments the unrefined plant extract containing sucrose as the main solute comprises an extract from a plant selected from the group comprising *Saccharum* species; *Saccharum officinarum*; *Agave* species; *Beta* species; *Beta vulgaris*; *Acer* species; *Cocos* species; *Arenga* species; *Nypa* species; *Phoenix* species; *Metroxylon* species; *Borassus* species; sweet sorghum varieties; and a mixture thereof.

In various embodiments the unrefined plant extract containing sucrose as the main solute comprises sugarcane juice partially processed prior to incubating with at least one microorganism.

As used herein 'partially processed' may refer to one or more operations such as filtration, clarification, boiling, crystallisation and/or centrifugation into unrefined forms of raw sucrose product such as jaggery. However, 'partially processed' may not refer to purifying technology such as affination and treatment with resins and/or activated charcoal. As such in the various embodiment that the unrefined plant extract containing sucrose as the main solute are partially processed the resulting product remains unrefined in that it is not pure, and is highly coloured compared to pure white refined sugars.

In various embodiments the various forms of sugarcane juice that have been produced by the mechanical crushing of sugarcane.

In various embodiments the unrefined plant extract containing sucrose as the main solute comprises sugarcane juice obtained from a *Saccharum* species; and at least one of jaggery, molasses, coconut sap, extract from palm species, or a combination thereof.

In various embodiments the unrefined plant extracts containing sucrose as the main solute may include any combination of sugarcane juice with other forms of sucrose such as jaggery, coconut sap or plant extracts from palm species, or molasses.

In various embodiments, the unrefined plant extract containing sucrose as the main solute may be derived from sugarcane including crude sugarcane juice, minimally processed sugarcane juice, clarified sugarcane juice and sugarcane syrup. As such, in various embodiments, the unrefined plant extract includes any sucrose-based plant extract, i.e. sucrose being the majority component present in the plant extract. In an example, the unrefined plant extract containing sucrose as the main solute includes sugar beet juice. The raw material may also be any other types of sugar-containing juices or syrups including sugar beet juice, high fructose corn syrup, maple syrup, agave nectar, agave syrup, brown rice syrup, other forms of sucrose containing extracts such as jaggery, coconut sap or plant extracts from palm species may be used in combination with sugarcane juice and any other sucrose/glucose/fructose/rhamnose/lactose-containing juice or syrup or blends thereof known in the art. In various embodiments the unrefined plant extract containing sucrose as the main solute may also be sap/juice/nectar/syrup obtained from trees including *Cocos nucifera, Arenga pinnata, Nypa fruticans, Phoenix dactylifera, Phoenix sylvestris, Metroxylon sagu* and members or the *Borassus* genus.

In alternative embodiments, the unrefined plant extract used as a feedstock or starting ingredient for the process of the present invention may include any glucose-based or fructose-based plant extract or a starch-hydrolysate derived product.

As used herein the term 'palm species' refers to plants in the Arecaceae family.

As used herein the term 'jaggery' refers to an unrefined extract from sugarcane that has been concentrated to a solid. The sugarcane juice may be partially processed by filtration, clarification, boiling, crystallisation and/or centrifugation in the making of jaggery. However, jaggery is not purified by technology such as affination and treatment with resins and/or activated charcoal. Jaggery may also be referred to as non-centrifugal sugarcane sugar.

In various embodiments the unrefined plant extract containing sucrose as the main solute comprises a sucrose carbon-13 to carbon-12 isotope ratio ($^{13}C/^{12}C$) of more than or equal to 11 parts per thousand, with a range of delta $^{13}C$ values of −5 and −20.

In various embodiments the unrefined plant extract containing sucrose as the main solute comprises an extract from a plant comprising a *Saccharum* species; a *Zea* species; or an *Agave* species and the sweetener comprises a sucrose carbon-13 to carbon-12 isotope ratio ($^{13}C/^{12}C$) of more than or equal to 11 parts per thousand, with a range of delta $^{13}C$ values of −5 and −20.

In various embodiments the unrefined plant extract containing sucrose as the main solute comprises sugarcane juices obtained from *Saccharum* species or *Saccharum officinarum*.

In various embodiments, unrefined plant extract containing sucrose as the main solute may comprise crude sugarcane juice that may be produced by shredding, milling and/or diffusion of sugarcane stalks or other sugar containing agricultural raw materials. In various embodiments, a minimally processed sugarcane juice may be produced from a crude sugarcane juice by pasteurisation and/or sulphite-treatment, optionally followed by filtration. In various embodiments, the clarified sugarcane juice may be produced from the minimally processed sugarcane juice by the use of liming, flocculation, absorbents, clarification, sedimentation and/or filtration.

In various embodiments the unrefined plant extract containing sucrose as the main solute is adjusted to a refractometric dry substance content of 8° Bx to 40° Bx prior to incubating with the microorganism.

As used herein the term 'adjusted' refers to dilution or concentration.

In various embodiments the sugar extract is adjusted to a refractometric dry substance content from 8° Bx to 40° Bx prior to incubating with the microorganism. In various other embodiments the unrefined plant extract containing sucrose as the main solute is adjusted to a refractometric dry substance content of 10° Bx to 35° Bx, or 15° Bx to 35° Bx or any suitable refractometric dry substance content for growing the microorganism.

In various embodiments the at least one microorganism comprises an osmo-tolerant and/or halo-tolerant microorganisms able to grow in a medium with a refractometric dry substance content of 8° Bx to 40° Bx.

In various embodiments the microorganism comprises an osmo-tolerant and/or a halo-tolerant microorganism able to grow in a medium with a refractometric dry substance content from 10° Bx to 40° Bx, 10° Bx to 35° Bx, or 15° Bx to 35° Bx, or 10° Bx to 20° Bx, or 12° Bx to 16° Bx.

In various embodiments the microorganism is selected from the group comprising bacteria; or fungi.

In various embodiments the fungi comprises yeast, or a *Klyveromyces* species or other forms of fungi.

In various embodiments the bacteria comprises or is selected from a gram positive strain or a gram negative strain. In various embodiments the bacteria is selected from the group comprising Xanthomonadaceae; Brevibacteriaceae; or Baccilaceae.

In various embodiments the microorganism comprises any one of *Stenotrophomonas maltophilia, Cellulosimicrobium cellulans, Bacillus subtilis, Bacillus flexus* or a *Klyveromyces* species or a combination thereof.

In various embodiments the microorganism comprises one or more selected from a group comprising *Stenotrophomonas maltophilia, Cellulosimicrobium cellulans, Bacillus subtilis*, or a *Klyveromyces* species and *Bacillus flexus* or a combination thereof.

In various embodiments the microorganism comprises one or more selected from a group consisting of *Stenotrophomonas maltophilia, Cellulosimicrobium cellulans, Bacillus subtilis*, or a *Klyveromyces* species and *Bacillus flexus* or a combination thereof.

In various embodiments the microorganism comprises a combination of at least two microorganisms. In various other embodiments the microorganism comprises a combination of at least three microorganisms.

In various embodiments the microorganism comprises a combination of at least two microorganisms incubated together as a mixed culture that act on the unrefined plant extract containing sucrose as the main solute to produce the modified unrefined plant extract.

In various embodiments the process further comprises the step of removing the microorganism or microorganisms and any biomass produced by the microorganism or microorganisms prior to heating the modified unrefined plant extract.

In various embodiments the removal may be done by filtration, centrifugation or any similar removal method. This has the advantage removing any contamination resulting in a clean flavoured sweetener.

In various embodiments the unrefined plant extract containing sucrose as the main solute may be incubated with the at least one microorganism in a controlled vessel wherein at least one of a temperature, a pH or a dissolved oxygen content is controlled during processing of the unrefined plant extract containing sucrose as the main solute. In such embodiments the incubation may be carried out in a controlled vessel. A controlled vessel is any vessel capable of controlling one or more operating parameters. In various embodiments the controlled vessel may be a bioreactor, an incubator or a double-jacketed steam vessel or any other scalable industrial vessel. In various embodiments the operating parameters may be temperature, pH, dissolved oxygen, biomass and/or concentration of any compound.

In various embodiments, the incubation in the controlled vessel is maintained in a hygienic environment and under biologically suitable conditions for the particular microorganism used for the incubation. In various embodiments the incubation may be an aerobic incubation. In various embodiments, the agitation may be from 0 rpm to 1800 rpm, or 100 rpm to 1200 rpm, or 200 rpm to 1800 rpm, or 400 rpm to 1800 rpm. In various embodiments, the gassing to maintain a suitable level of dissolved oxygen may comprise any amount suitable for the microorganism used. In various embodiments the gassing may comprise between 0 vvm (volume gas per volume medium per minute) to 2 vvm, or 0.1 vvm to 1 vvm, or 0.1 vvm to 0.5 vvm, or 0.1 vvm to 0.3 vvm. In various embodiments, the pH range may be any biologically relevant range suitable for the microorganism used in the incubation. In various embodiments the pH range may comprise 3.9 to 7.5, with or without the addition of sodium carbonate to adjust pH. In various embodiments, the temperature of the incubation may comprise any temperature suitable for the microorganism used. In various embodiments, the temperature of the incubation may comprise 20° C. to 40° C. In various embodiments, the incubation time may comprise any time suitable for the microorganism metabolism and may comprise from 1 hour to 24 hours.

In various embodiments the process further comprises a second incubation of the modified unrefined plant extract with a second microorganism. In various embodiments the second incubation may be sequential. In various embodiments the first incubation may comprises an incubation with one or more microorganisms, followed by a subsequent second inoculation with one or more microorganisms in the second incubation.

In various embodiments the process further comprises heating the modified unrefined plant extract to evaporate water and form a concentrate and cooking the concentrate at a temperature above the boiling point to form a viscous syrup or solid product.

In various embodiments cooking the concentrate develops flavour and colour whereby volatile chemicals are released.

In various embodiments the modified unrefined plant extract is heated and cooked until reaching a temperature and refractometric dry substances content of 80° C. to 170° C. and 50° Bx to 100° Bx, or especially 110° C. to 130° C. and 75° Bx to 95° Bx and particularly up to approximately 120° C. and 90° Bx so as to form a viscous syrup or solid product.

In various embodiments the process further comprises the step of reducing the sucrose concentration of the flavoured sweetener or reducing the sucrose concentration of a coconut sugar.

In various embodiments the step of reducing the sucrose concentration of the flavoured sweetener comprises crystallising the flavoured sweetener and performing selective washing thereby separating the flavoured sweetener syrup from the sucrose crystals that remain. This general method includes affination.

In various embodiments, the flavoured sweetener may be aged and matured for a period ranging for 1 day to 2 months prior to use. In various embodiments the colour, texture, aroma and flavour of sweetener may be stabilised or enhanced by using additives including coconut sugar, colourants, colour retention agents, antioxidants, anti-caking agents, oils, humectants, drying agents, acidity regulators, preservatives, flavour molecules and mixtures of flavour molecules, flavour extracts, flavour enhancers such as monosodium glutamate, plant extracts and sweeteners, and maltol.

In various embodiments the process further comprises the step of mixing the flavoured sweetener with other sweeteners.

This has the advantage of forming a blended flavoured sweetener. In various embodiments the other sweeteners may comprise coconut sugars, jaggery or any other sweetener that will allow the flavoured sweetener to maintain its characteristic flavour.

In various embodiments the process further comprises the step of making a flavour extract by isolating one or more flavour molecules from the modified unrefined plant extract or the flavoured sweetener or the syrup of the flavoured sweetener, or the crystal phase of the flavoured sweetener or a coconut sugar.

In various embodiments the one or more flavour molecules comprise any one of 3-Hydroxy-4,5-dimethyl-2(5H)-furanone; 4-Hydroxy-3-methoxybenzaldehyde; 4-Hydroxy-2,5-dimethyl-3(2H)-furanone; 3-Methylsulfanylpropanal; Acetic acid; 2-Methylbutanoic acid/3-methylbutanoic acid; 2-Phenylpropionic acid/3-Phenylpropionic acid; Phenylacetic acid; 2-Methoxy-4-prop-1-en-2-ylphenol; (E)-1-(2,6,6-Trimethyl-1-cyclohexa-1,3-dienyl)but-2-en-1-on; 2-Methylbutanal/3-Methylbutanal; (E)-3-[(2S,3R)-3-Pentyloxiran-2-yl]prop-2-enal; 2-Methoxy-4-prop-2-enylphenol; or 2-methoxyphenol.

This novel process and product is also a source of natural flavour molecules as it uses microorganism metabolism either by bio-catalytic or metabolic processes to generate flavour molecules. In various embodiments the one or more isolated flavour molecules may be used to flavour other sweeteners to produce a flavoured sweetener with the desired characteristics of coconut sugar Another aspect of the invention provides a modified unrefined plant extract derivable by the method comprising, incubating an unrefined plant extract containing sucrose as the main solute with a microorganism or microorganisms to form a modified unrefined plant extract.

In various embodiments the unrefined plant extract containing sucrose as the main solute comprises any one defined in any one of the embodiments described above and the at least one microorganism comprises any one defined in any one of the embodiments described above.

Another aspect of the invention provides a flavoured sweetener derivable by the process disclosed herein, further comprising: a first characteristic comprising at least one selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 5 or greater; and (E)-1-(2,6,6-trimethyl-1-cyclohexa-1,3-dienyl)but-2-en-1-one present at a flavour dilution number of at least 8; a second characteristic comprising at least one selected from glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %; and; a third characteristic comprising at least one selected from the group comprising: 3-Hydroxy-4,5-dimethyl-2(5H)-furanone at a flavour dilution number of at least 10, 4-Hydroxy-3-methoxybenzaldehyde at a flavour dilution number of at least 7, 4-Hydroxy-2,5-dimethyl-3(2H)-furanone at a flavour dilution number of at least 5, 3-Methylsulfanylpropanal, Acetic acid, 2-Methylbutanoic acid/3-methylbutanoic acid, 2-Phenylpropionic acid/3-Phenylpropionic acid, Phenylacetic acid, 2-Methoxy-4-prop-1-en-2-ylphenol, (E)-1-(2,6,6-trimethyl-1-cyclohexa-1,3-dienyl)but-2-en-1-one, 2-Methylbutanal/3-Methylbutanal, (E)-3-[(2S,3R)-3-Pentyl oxiran-2-yl]prop-2-enal, 2-methoxy-4-prop-2-enylphenol, and 2-Methoxyphenol.

In various embodiments first characteristic comprises at least two, at least three, at least four, at least five, at least six, selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 5 or greater; and (E)-1-(2,6,6-trimethyl-1-cyclohexa-1,3-dienyl)but-2-en-1-one present at a flavour dilution number of at least 8; In various embodiments the flavoured sweetener comprises any one of a syrup, paste, amorphous or semi-crystalline solid in bulk, lump or granular form.

In various embodiments second characteristic comprises: glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %.

In various embodiments third characteristic comprises at least two, at least three, at least four, at least five, at least six, at least seven; at least eight; at least nine; at least ten; at least eleven; at least twelve; at least thirteen; or at least fourteen; selected from the group comprising: 3-Hydroxy-4,5-dimethyl-2(5H)-furanone; 4-Hydroxy-3-methoxybenzaldehyde; 4-Hydroxy-2,5-dimethyl-3(2H)-furanone; 3-Methylsulfanylpropanal; Acetic acid; 2-Methylbutanoic acid/3-methylbutanoic acid; 2-Phenylpropionic acid/3-Phenylpropionic acid; Phenylacetic acid; 2-Methoxy-4-prop-1-en-2-ylphenol; (E)-1-(2,6,6-Trimethyl-1-cyclohexa-1,3-dienyl)but-2-en-1-on; 2-Methylbutanal/3-Methylbutanal; (E)-3-[(2S,3R)-3-Pentyloxiran-2-yl]prop-2-enal; 2-Methoxy-4-prop-2-enylphenol; or 2-methoxyphenol.

In various embodiments the reduced sucrose flavoured sweetener comprises a sucrose content of below 40 wt %.

In various embodiments the reduced sucrose flavoured sweetener comprises a sucrose content of 10 wt % to 40 wt %.

Another aspect of the invention provides a flavour extract derivable by the process as described herein comprising at least ten of the flavour molecules selected from the group comprising: 3-Hydroxy-4,5-dimethyl-2(5H)-furanone; 4-Hydroxy-3-methoxybenzaldehyde; 4-Hydroxy-2,5-dimethyl-3(2H)-furanone; 3-Methylsulfanylpropanal; Acetic acid; 2-Methylbutanoic acid/3-methylbutanoic acid; 2-Phenylpropionic acid/3-Phenylpropionic acid; Phenylacetic acid; 2-Methoxy-4-prop-1-en-2-ylphenol; (E)-1-(2,6,6-Trimethyl-1-cyclohexa-1,3-dienyl)but-2-en-1-on; 2-Methylbutanal/3-Methylbutanal; (E)-3-[(2S,3R)-3-Pentyloxiran-2-yl]prop-2-enal; 2-Methoxy-4-prop-2-enylphenol; or 2-methoxyphenol; or a combination thereof.

In various embodiments the flavour extract comprises at least ten, at least eleven; at least twelve, at least thirteen; at least fourteen flavour molecules selected from the group consisting of 3-Hydroxy-4,5-dimethyl-2(5H)-furanone; 4-Hydroxy-3-methoxybenzaldehyde; 4-Hydroxy-2,5-dimethyl-3(2H)-furanone; 3-Methylsulfanylpropanal; Acetic acid; 2-Methylbutanoic acid/3-methylbutanoic acid; 2-Phenylpropionic acid/3-Phenylpropionic acid; Phenylacetic acid; 2-Methoxy-4-prop-1-en-2-ylphenol; (E)-1-(2,6,6-Trimethyl-1-cyclohexa-1,3-dienyl)but-2-en-1-on; 2-Methylbutanal/3-Methylbutanal; (E)-3-[(2S,3R)-3-Pentyloxiran-2-yl]prop-2-enal; 2-Methoxy-4-prop-2-enylphenol; or 2-methoxyphenol.

Another aspect of the invention provides a process or method for manufacturing a food product, comprising: (a) incubating an unrefined plant extract containing sucrose as the main solute with a microorganism or microorganisms to form a modified unrefined plant extract; (b) heating the modified unrefined plant extract to produce a flavoured sweetener; (c) mixing the flavoured sweetener with an additional ingredient; and (d) forming the food product.

The term 'food product' as used herein refers to any product that can be consumed, eaten or drunken by an animal such as a mammal, particularly a human. This includes foods and beverages that can be consumed, eaten or drunken by an animal.

The described process or method for manufacture reduces processing costs and achieves economies of scale, superior product quality control of the product and without adulterating additions of preservative chemicals and simplification of supply chains from farm gate to the fork of the consumer.

Thus the flavoured sweetener can overcome the supply constraints and especially meet the expanding demands for food products such as sweet sauce, chocolates, sweets and other product that traditionally use coconut sugar as an ingredient while being consistent with the quality standards of the existing products. The flavoured sweetener also has the potential to find uses in a wide range of other food and beverage applications that hitherto have been constrained by the shortages in supply and higher costs of traditional coconut sugar. In various embodiments the food product may comprise other food and beverage applications such as in snacks, confections, desserts, carbohydrate-based cooked foods like buns, rice and noodles, processed foods, dips, soups, gravies, stews, curries, spreads, jams, syrups, dressings, marinated food products, fried products, baked products, energy bars, beverages such as coffees, tea, energy drinks, malt-drinks, concentrates, sweet drinks, pet foods, and all other food applications which utilize condiments such as sweet soy sauce. In particular chocolate can be made by combining the flavoured sweetener or reduced sucrose flavoured sweetener with cocoa powder, water and other ingredients, optionally milk, cocoa butter, nuts, fruit and other inclusion ingredients, flavourings such as toffee and coffee, vanillin and/or vanilla and emulsifiers.

In various embodiments the process or method for manufacture further comprises reducing the sucrose content of the flavoured sweetener prior to adding the ingredient.

In various embodiments the additional ingredient comprises sauce.

In various embodiments the additional ingredient comprises soy sauce.

In various embodiments the additional ingredient comprises a salt solution plus acetic acid or vinegar.

In various embodiments the additional ingredient comprises spices, plant extracts; flavours; or flavour enhancers or flavour extracts and/or flavour molecules.

In various embodiments the additional ingredient comprises further comprises flour or starch and oil, preferably vegetable oil.

In various embodiments the additional ingredient comprises sweeteners with a low glycemic index, isomalt, isomaltulose or D-tagatose. Isomalt, isomaltulose and D-tagatose comprise examples of sweeteners with a low glycemic index.

In various embodiments the additional ingredient comprise any one of chocolate; dried fruits; ginger; seeds; nuts; milk; cream; custard; butter; cocoa; milo; vinegar, vegetable or meat chilli; onion; garlic; ginger; lemongrass; tamarind; turmeric; cinnamon; coriander; or pepper or meat.

In various embodiments the process or method for manufacture further comprises the step of heating the mixture prior to forming the food product.

In various embodiments the process for making the flavoured sweetener can be extended also into the method for manufacture of food products as described herein.

In various embodiments the food product comprises sweet sauce. In various embodiments the sweet sauce is made into a powder or paste wherein the additive further comprises flour or starch and/or vegetable oil. Any suitable starch based flour would be suitable such as wheat flour, potato flour, corn flour, tapioca flour, or any other starch based flour known in the art.

In various embodiments, a sweet sauce product may be produced by combining the flavoured sweetener produced as described herein and additional ingredients such as water, salt solution, vinegar, soy sauce, traditionally produced CNS, or sweet sauces, flavour enhancers such as monosodium glutamate, spices, plant extracts, flavourings, flavoured extracts, flavour molecules and mixtures of flavour molecules, flour, starch-based ingredients, vegetable oils, preservatives, antioxidants and colourings such as caramel with or without an additional heating process. In various embodiments the sweet soy sauce product may be in the form of a sauce, dips, syrup, paste or powder.

As used herein the term 'sweet sauce' refers to a sweet salty sauce comprising a sweetener produced as described herein, water, and soy sauce.

As used herein the term 'spicy sweet sauce' refers to a spicy sweet salty sauce comprising a sweetener produced as described herein, water, chili, garlic and soy sauce.

As used herein the term 'onion sweet sauce' refers to a garlic and onion sweet salty sauce comprising a sweetener produced as described herein, water, garlic, onion and soy sauce. In various embodiments the onion is red onion.

Another aspect of the invention provides a food product derivable by the process or method for manufacturing a food product as described herein comprising: a first characteristic comprising at least one selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 0.5 or greater; and (E)-1-(2,6,6-trimethyl-1-cyclohexa-1,3-dienyl)but-2-en-1-one present at a flavour dilution number of at least 8; a second characteristic comprising at least one selected from glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %; and; a third characteristic comprising at least one selected from the group comprising: 3-Hydroxy-4,5-dimethyl-2(5H)-furanone at a flavour dilution number of at least 10, 4-Hydroxy-3-methoxybenzaldehyde at a flavour dilution number of at least 7, 4-Hydroxy-2,5-dimethyl-3(2H)-furanone at a flavour dilution number of at least 5, 3-Methylsulfanylpropanal, Acetic acid, 2-Methylbutanoic acid/3-methylbutanoic acid, 2-Phenylpropionic acid/3-Phenylpropionic acid, Phenylacetic acid, 2-Methoxy-4-prop-1-en-2-ylphenol, (E)-1-(2,6,6-trimethyl-1-cyclohexa-1,3-dienyl)but-2-en-1-one, 2-Methylbutanal/3-Methylbutanal, (E)-3-[(2S,3R)-3-Pentyl oxiran-2-yl]prop-2-enal, 2-methoxy-4-prop-2-enylphenol, and 2-Methoxyphenol wherein the first, second and third characteristics are proportional to the flavoured sweetener content of the food product.

In various embodiments the food product further comprises a sweetener with a low glycemic index, isomalt, isomaltulose or D-tagatose. Isomalt, isomaltulose and D-tagatose comprise examples of sweeteners with a low glycemic index.

In various embodiments the food product comprises flavoured sweetener or reduced sucrose flavoured sweetener combined with cocoa powder, or chocolate liquor, water or cocoa butter and other ingredients comprising chocolate optionally milk, cocoa butter, nuts, fruit, flavourings, vanillin, or vanilla, coffee, toffee, or emulsifiers, lecithin or polyglycerol polyricinoleate.

In various embodiments the food product further comprises any one of chocolate; dried fruits; ginger; seeds; nuts; milk; cream; custard; butter; cocoa; milo; vinegar, vegetable or meat chilli; onion; garlic; ginger; lemongrass; tamarind; turmeric; cinnamon; coriander; or pepper.

In various embodiments the food product further comprises an additional ingredient.

In various embodiments the additional ingredient comprises spices, plant extracts; flavours; or flavour enhancers or flavoured sweeteners.

In various embodiments the additional ingredient comprises a sauce.

In various embodiments the additional ingredients comprise soy sauce or a sweet soy sauce.

In various embodiments the additional ingredients comprise a salt solution and acetic acid or vinegar.

In various embodiments the additional ingredient comprises any of tempeh, or green beans.

In various embodiments the additional ingredient comprises any one of chilli, garlic, soy sauce, green beans, onions, maize, carrots, potato or chicken.

In various embodiments the food product further comprises flour and/or starch.

In various embodiments the food product further comprises an oil, preferably vegetable oil.

Another aspect of the invention provides a sweet sauce derivable by the process or method for manufacturing a food product as described herein, the sweet sauce comprising a first characteristic comprising at least one selected from the group comprising: a sucrose content of at least 40 wt %; a sucrose carbon-13 to carbon-12 isotope ratio ($^{13}C/^{12}C$) of more than or equal to 11 parts per thousand, with a range of delta $^{13}C$ values of −5 and −20; an isotope ratio of the molecules aconitic acid, glutamic acid, monosodium glutamate, guanosine monophosphate, inosine monophosphate, disodium guanylate and disodium inosinate molecules, and an aroma chemical molecule consisting of a carbon-13 to carbon-12 isotope ratio ($^{13}C/^{12}C$) of more than or equal to 11 parts per thousand, with a range of delta $^{13}C$ values of −5 and −20; aconitic acid present at greater than 0.1 wt %; a potassium to sodium weight by weight ratio of 0.5 or greater; and (E)-1-(2,6,6-trimethyl-1-cyclohexa-1,3-dienyl)but-2-en-1-one present at a flavour dilution number of at least 8; a second characteristic comprising at least one selected from glutamic acid and monosodium glutamate present at a combined concentration greater than 0.1 wt %; or guanosine monophosphate, inosine monophosphate, disodium guanylate and disodium inosinate present at a combined concentration of greater than 0.1 wt %; and; a third characteristic comprising at least one selected from the group comprising: 3-Hydroxy-4,5-dimethyl-2(5H)-furanone at a flavour dilution number of at least 10, 4-Hydroxy-3-methoxybenzaldehyde at a flavour dilution number of at least 7, 4-Hydroxy-2,5-dimethyl-3(2H)-furanone at a flavour dilution number of at least 5, 3-Methylsulfanylpropanal, Acetic acid, 2-Methylbutanoic acid/3-methylbutanoic acid, 2-Phenylpropionic acid/3-Phenylpropionic acid, Phenylacetic acid, 2-Methoxy-4-prop-1-en-2-ylphenol, (E)-1-(2,6,6-trimethyl-1-cyclohexa-1,3-dienyl)but-2-en-1-one, 2-Methylbutanal/3-Methylbutanal, (E)-3-[(2S,3R)-3-Pentyl oxiran-2-yl]prop-2-enal, 2-methoxy-4-prop-2-enylphenol, and 2-Methoxyphenol wherein the first, second and third characteristics are proportional to the flavoured sweetener content of the sweet sauce.

In various embodiments the sweet sauce further comprises, reduced sucrose flavoured sweetener, low glycemic index flavoured sweetener or additionally flavoured sweetener, additionally flavoured reduced sucrose flavoured sweetener, or additionally flavoured low glycemic index flavoured sweetener, coconut sugar or jaggery flour and/or starch or vegetable oil or any combination thereof.

Another aspect of the invention provides a process of reducing the sucrose content in a flavoured sweetener comprising affination, filtration, centrifugation or solvent extraction.

In various embodiments the flavoured sweetener used in the process for reducing the sucrose comprises any one of the flavoured sweetener described herein, or a coconut sugar.

In various embodiments the process for reducing the sucrose further comprises adding a sweetener with a low glycaemic index to the reduced sucrose flavoured sweetener.

Throughout this document, unless otherwise indicated to the contrary, the terms "comprising", "having" and the like, are to be construed as non-exhaustive, or in other words, as meaning "including, but not limited to".

Furthermore, throughout the specification, unless the context requires otherwise, the word "include" or variations such as "includes" or "including" will be understood to imply the inclusion of a stated integer or group of integers but not the exclusion of any other integer or group of integers.

As used in the specification, the singular form "a", "an" and "the" include plural references unless the context clearly dictates otherwise.

Unless defined otherwise, all technical and scientific terms used herein have the same meaning as is commonly understood by a skilled person to which the subject matter herein belongs.

It should be further appreciated by the person skilled in the art that variations and combinations of features described above, not being alternatives or substitutes, may be combined to form yet further embodiments falling within the intended scope of the invention.

EMBODIMENTS

The current market consists of a range of CNSs and sweet sauces with different flavour characteristics and chemical compositions that have developed semi-independently over many years and now continue to be made and used to meet local preferences.

To meet this demand for a range of different flavoured sweeteners and sweet sauce products a versatile process has been developed that can accommodate a range of modifications so as to produce these ranges of product required by customers with different preferences.

Moreover, the new process uses abundantly available natural food quality sugar-containing raw materials such as sugarcane juice from cultivated *Saccharum* species, which are produced on a much larger scale and at higher productivities per hectare than coconut inflorescence sap. Therefore, the flavoured sweeteners and sweet sauces made from it can be made available at a significantly lower cost than traditional CNSs and sweet sauces.

This versatile new process is based on three critical unit operations: incubation, evaporation and cooking of the unrefined plant extract containing sucrose as the main solute. After cooking the flavoured sweetener can be cooled and obtained in a syrup, paste, amorphous or semi-crystalline solid in bulk, lump or granular form. This flavoured sweetener product can be used for making sweet sauce by heating with soy sauce, as a source of natural flavour extracts and flavour molecules, and in lower sucrose and reduced glycaemic index forms. The sweet sauce can be further processed into a powder or paste form.

The Process
Raw Material

The substrate for the incubation and raw material for the flavoured sweetener is an unrefined plant extract containing sucrose as the main solute. This extract can be from sugar crops such as sugarcane, sugar beet, sweet sorghum and agave; trees such as coconut palm, palmyra palm, date palm, sugar date palm and maple tree; and fruits such as apricot, banana, mango, nectarine and/orange. The flavour profile of the flavoured sweetener depends strongly on the raw material. In an example, the raw material may be sugar beet juice.

The raw material for a coconut sugar is coconut palm inflorescence sap, and as the traditional product is generally regarded as setting the product standards such as for flavour quality. The process outlined herein can produce a high quality coconut sugar substitute by a controlled and optimised incubation and cooking process which ensures a consistently high quality product. To solve the supply limitations, poor scalability and high price of coconut palm inflorescence sap, sugarcane juice has now been identified as the overall best raw material. In the case of sugarcane the juice is extracted by first shredding the sugarcane stalks, then milling and/or diffusing out the sugar.

The raw material being unrefined refers to not having undergone processes such as affination and treatment with resins and activated charcoal as in the production of white refined sugar. Using a refined plant extract, such as pure sucrose or glucose in water with micronutrients does not produce a flavoured sweetener of acceptable flavour quality by the process outlined herein. Using an unrefined plant extract containing sucrose as the main solute as a raw material confers advantages such as the incubation not needing additional micronutrients and a better and more natural flavour of the flavoured sweetener. The unrefined plant extract containing sucrose as the main solute can be either crude or partially processed by one or more unit operations such as filtration, clarification, boiling, crystallisation and centrifugation. The by-product of centrifugation and refining is sugarcane molasses, which used alone does not produce a flavoured sweetener of acceptable quality, but when mixed with sugarcane juice an acceptable product can be obtained as in Example 4.

As well as providing sweetness to the flavoured sweetener, the sucrose present as the main solute, in contrast to glucose and fructose, is less deliquescent, allowing for a relatively dry flavoured sweetener product with high osmotic pressure and therefore good shelf-life.

Thus making a good quality coconut sugar substitute product is possible using an unrefined plant extract containing sucrose as the main solute from sugarcane, such as sugarcane juice (Example 1 and Example 2) jaggery (Example 3), sugarcane juice mixed with sugarcane molasses (Example 4) and sugarcane syrup (Example 5).

The Microorganisms

The microorganisms used herein are aerobic, as they grow well in aerobic conditions, osmotolerant as they grow in media with high osmotic pressures, and they modify the unrefined plant extract containing sucrose as the main solute so that it produces a coconut sugar-like flavour when heated. By "microorganism", it is meant to include any single-celled or multi-cellular microbe (whether naturally occurring or produced through recombinant DNA technology). In addition, it is also meant to include any cell that can carry out the incubation process described in the present invention. These cells may be living (whether naturally occurring or produced through recombinant DNA technology), artificial cells, cell ghosts, or pseudovirions, to serve any of several purposes.

By "artificial cell" or a minimal cell, it is meant to include any engineered particle that mimics one or many functions of a biological cell that may be created to contain metabolic pathways needed to produce all of the flavour molecules and flavour precursors that can create a coconut sugar substitute-like flavour of the present invention.

The microorganisms may be used in either mobile or immobilised forms, such as in carrageenan or alginate pellets.

The microorganisms may be used in a monoculture or in a mixed culture. A better flavour can be obtained by using mixed cultures of complimentary different microbial species.

The microorganisms comprise a group containing *Stenotrophomonas maltophilia*, *Cellulosimicrobium cellulans*, *Bacillus subtilis*, *Bacillus flexus* and *Kluyveromyces* species. Binary mixed cultures of *Stenotrophomonas maltophilia* & *Bacillus flexus* are used in Example 1, Example 4 and Example 8, *Bacillus subtilis* & *Bacillus flexus* in Example 2, Example 3 and Example 5. A monoculture of *Kluyveromyces* species is used in Example 6.

Incubation

Incubation may be carried out in any suitable medium. In various embodiments, a defined media approach may be taken. A defined fermentation medium is one in which only those chemically defined components required for the growth of the microorganisms or cells and their production of the desired product are present, and in quantities that are optimal. The development of defined media is a standard approach used in fermentation technology, usually to reduce the cost of the production media used, and thus to reduce overall manufacturing costs. Coconut sap and sugar cane juice may be analysed to identify all of the molecules that contribute to the growth of the microbial strains and that act as raw materials of the flavour molecules and flavour precursor molecules needed to make a coconut sugar substitute of the present invention. Then carrying out a fermentation using this medium, followed by heating of the fermented defined medium. This approach also has the advantage of not necessarily requiring as much sucrose as is present in the fermented product, so that only the amount of sucrose need be added to best suit the end-use products.

The incubation is performed hygienically, i.e. pasteurising the unrefined plant extract containing sucrose as the main solute and inoculating with selected microorganisms. The operating conditions of the incubation such the refractometric dry substance (RDS), time, temperature, pressure, pH, agitation, gassing and dissolved oxygen concentration can be varied to reduce processing time and/or modify the flavour of the flavoured sweetener.

An aerobic incubation can be operated in the ranges of RDS from 8° Bx to 30° Bx, time from 1 hour to 24 hours, temperature from 20° C. to 40° C., pressure from 1 bar to 5 bar, pH from 4 to 10, linear tip speed from 0 m/s to 10 m/s, gassing from 0 vvm to 2 vvm (volume gas per volume medium per minute) and a relative dissolved oxygen concentration from 20% to 100%.

For making a coconut sugar substitute product a sugarcane extract with a RDS in the range of 12° Bx to 16° Bx, pH around 6, temperature of 33° C., incubation time in the range of 3 to 5 hours and dissolved oxygen concentration of 30% is optimal in regards to microbial growth speed and flavour of the resulting flavoured sweetener.

The effect of incubation time is tested in Example 2 for the combination of the microbial strains *Bacillus subtilis*, and *Bacillus flexus*. The quality of the flavoured sweetener produced from the modified unrefined plant extract increases during the incubation, peaking at around 3 to 4 hrs, and then declines. This decline in flavoured sweetener quality is associated with a comparatively sudden loss of any viable *Bacillus flexus* cells, which had risen from a concentration at inoculation of around $5.5 \times 10^5$ CFU/mL to a concentration of $4.0 \times 10^6$ CFU/mL after 3 hrs incubation, whereas viable cell counts for the *Bacillus subtilis*, had begun at around $7.5 \times 10^5$ CFU/mL, rose to $1.6 \times 10^7$ CFU/mL after 3 hrs, but unlike the *Bacillus flexus*, *Bacillus subtilis*, continued to grow, reaching a concentration of $3.1 \times 10^8$ CFU/mL after 5 hrs, well after no viable *Bacillus subtilis* cell had last been detected, but only resulting in a different tasting product of lower quality. Thus the change in flavoured sweetener quality is related to changes in the microbiology of the incubation over time.

The microbial biomass and microbially produced biomass can optionally be removed by centrifugation or filtration prior to cooking to produce a different flavour profile of the flavoured sweetener.

The product of the incubation process is referred to as a modified unrefined plant extract, and may be stabilised against microbial activity such as by concentration, heating, cooling, or addition of chemicals before further use.

Evaporation

Evaporation is the process of removing water from the modified unrefined plant extract until it is has a concentration suitable for entering the flavour generating cooking process, which is generally means a RDS about 60° Bx to 70° Bx, but a lower RDS, e.g. down to 20° Bx, can be suitable for specialty products. In Example 1 to Example 4 the evaporation is performed in an open-pan analogous to the traditional method of making CNS. On an industrial scale more energy-efficient evaporation can be achieved by using natural circulation evaporators, forced circulation evaporators, plate evaporators, falling-film evaporators and/or rising-film evaporators.

Cooking

The cooking process is distinguished from the evaporation in that process is where flavour generation by the Maillard reaction and caramelisation reaction takes place, due to the higher temperatures and/or concentrations employed. The operating variables are the RDS, time, temperature, pressure, pH, agitation, gassing, and the addition of flavour precursors such as rhamnose, flavour molecules such as 4-hydroxy-2,5-dimethyl-3(2H)-furanone, 3-hydroxy-2-methyl-4(4H)-pyranone and/or 4-hydroxy-3-methoxybenzaldehyde and complementary products, such as other CNSs and/or molasses.

In an open-pan process the pressure is fixed at 1 atmosphere and the RDS, time and temperature are dependent variables linked by the pan surface area and effect, and the colligative (i.e. boiling point elevation) properties of the incubation product.

In an open-pan process, depending on the interdependent variables of RDS, time and temperature the form of the flavoured sweetener product can be controlled. A flavoured sweetener syrup can be made from incubated sugarcane juice at approximately 50° Bx to 75° Bx and 102° C. to 110° C., a paste at approximately 80° Bx and 115° C. and a solid product can be made at approximately 90° Bx to 95° Bx and 120° C. The solid can be made amorphous merely by cooling (Example 1 to Example 4), or semi-crystalline either by vigorous stirring (Example 2) or by seeding with sucrose crystals while cooling. The total energy consumption for evaporation and cooking is approximately 2,300 kJ/kg of incubated sugarcane juice without taking into account any heat loss or heat of crystallisation.

The best processing conditions for an open-pan process when the unrefined plant extract containing sucrose as the main solute is sugarcane juice are found to be approximately 120° C., 90° Bx and 60 minutes evaporation time followed by 30 minutes cooking time. The evolution of temperature, RDS and pH over time in an open-pan evaporation and cooking process of an incubated sugarcane juice is shown in FIG. 1.

In an industrial process using equipment such as vacuum pans, pressurised vessels, or scraped surface heat exchangers, the RDS and temperature can be controlled independently of each other by adjusting the pressure, meaning that there is no lower limit of the RDS. Vacuum pans can readily operate at a RDS up to 85° Bx and temperature down to 65° C., and a steam-heated pressurised cooking vessel can readily operate at 90° Bx and 130° C., while a RDS of 100° Bx and temperatures as high as 170° C. can be reached in a scraped surface heat exchanger, where high viscosity and burn-on effects are reduced.

Optionally a more highly flavoured sweetener product can be made by heating to higher temperatures than 120° C. so as to enhance for example its burnt flavour notes. This second flavoured sweetener product can be used as a flavouring ingredient especially to add to the flavoured sweetener product as produced herein so as to boost certain flavour characteristics.

Optionally the flavours of the flavoured sweetener products can be enhanced either by the addition of one or more flavour precursors, such as cysteine, rhamnose and threonine to produce furanone flavour characteristics, by entering into flavour development reactions during the cooking process, or by the addition of one or more flavour molecules, such as 4-Hydroxy-3-methoxybenzaldehyde to improve the taste of the flavoured sweetener.

Optionally the flavoured sweetener may be matured for further flavour development. The maturation may take 1 day to 2 months.

Sweet Sauce Preparation

The flavoured sweetener may be used to make a sweet sauce, and this product is referred to as a sweet sauce made with flavoured sweetener when it needs to be distinguished from other sweet sauces. The sweet sauce so produced can be made either from a previously produced flavoured sweetener by heating and mixing with salt water (Example 7) or soy sauce. The sweet sauce can also be prepared in a 'one-pot' process where the salt water or soy sauce is added to the flavoured sweetener at the end of the cooking process as in Example 8. Flavour generation may take place during this heating and mixing process, and the operating variables are soy sauce dosage, RDS, time, temperature, pressure, pH, agitation and the addition of flavour precursors such as rhamnose, flavour molecules such as 4-hydroxy-2,5-dimethyl-3(2H)-furanone, 3-hydroxy-2-methyl-4(4H)-pyranone, 4-hydroxy-3-methoxybenzaldehyde and acetic acid (Example 7) and complementary products, such as jaggery, other flavoured sweeteners, CNSs and/or molasses.

The dosage of soy sauce used depends on the sweet to salty balance wanted in the sweet sauce made with flavoured sweetener, and ranges from approximately 20 wt % to 100 wt %. The cooking temperature is 80° C. to 110° C. for a duration of 10 minutes to 2 hours.

The best processing conditions for a 'one-pot' open-pan process when the unrefined plant extract containing sucrose as the main solute is sugarcane juice has added to it an approximate soy sauce dosage of approximately 25 wt % of the sweet sauce made with flavoured sweetener, addition of an amount of tap water equivalent to the soy sauce amount to balance the water evaporated in the process, cooking temperature of 80° C. for 60 minutes yielding a viscous sauce with a RDS of approximately 80° Bx, as in Example 8.

The sweet sauce so produced can also be used in combination with healthy herbs, flowers, leaves, roots, fruits and other plant extracts, such as found in traditional Chinese or Indonesian medicine (jamu). These healthy ingredients include ginger, galangal, curcumin, cinnamon, turmeric, fenugreek, tamarind, blueberries and grapes. The active molecules in these healthy ingredients anthocyanins, may also be added directly into the sweet sauce made with flavoured sweetener.

Optionally the sweet sauce so produced may be matured for further flavour development. The maturation may take 1 day to 2 months.

Powder or Paste Formulation

The flavoured sweetener produced by the processes described herein or CNSs produced by traditional processes can be formulated as a dry powder, or paste capable of being shaped into stock cubes for example. Dry powder flavoured sweetener is made by mixing at low speed a flavoured sweetener prepared as described hereinto with approximately 20 wt % to 40 wt % starch or flour at approximately 80° C. to 120° C. followed by drying and grinding. Paste flavoured sweetener can be made in a similar manner with approximately 0 wt % to 20 wt % starch or flour at approximately 80° C. to 120° C. followed by drying and grinding. The starch or flour used can be based on wheat, potato, tapioca, corn or other starch-containing plants. This product can also be prepared from CNS. This type of product is exemplified in Example 11.

Sweet sauces whether produced by the processes described herein or by traditional processes can also be formulated as a dry powder or paste capable of being shaped into e.g. stock cubes. Dry powder sweet sauce is made by mixing at low speed sweet sauce prepared as described hereinto with approximately 50 wt % to 70 wt % starch or flour at ambient temperature. Paste sweet sauce can be made in a similar manner by stir frying an approximately 30 wt % to 50 wt % starch or flour and vegetable oil and mixing in the sweet sauce. The starch or flour used can be based on wheat, potato, tapioca, corn or other starch-containing plants. This type of product can also be prepared from commercial sweet sauces, and is suitable for use in stock cubes or lozenges. The products are also exemplified in Example 11.

Reduced Sucrose Flavoured Sweeteners

The methods outlined herein can also be used to make reduced sucrose flavoured sweeteners and natural flavour extracts from the modified unrefined plant extract, flavoured sweeter or sweet sauce made with flavoured sweetener, such as by affination, filtration, centrifugation or solvent extraction.

An affination-like method using filtration to produce a reduced sucrose flavoured sweetener is shown in Example 9, where the sucrose crystals in a semi-crystalline flavoured sweetener are separated from the amorphous matrix by washing with a mixture of ethanol and water. It is estimated that one third of the sucrose is removed by this process, corresponding to approximately 15 wt % of the total mass of the flavoured sweetener.

Low glycaemic index sweeteners such as isomalt, isomaltulose or tagatose may be added to these reduced sucrose flavoured sweeteners to increase their sweetness without increasing their GI potential or cariogenicity.

Natural Flavour Extracts

The methods outlined herein can also be used to make natural flavour extracts and/or natural flavour or fragrance chemicals from the modified unrefined plant extract, flavoured sweeter or sweet sauce made with flavoured sweetener, such as by solvent extraction, supercritical $CO_2$ extraction, distillation, condensation of gases, dialysis, absorption, adsorption, filtration or spinning cone processes A solvent extraction method for making a natural flavour extract using diethyl ether is shown in Example 10.

The Products

Overview

Flavoured sweetener A (FS-A) was made in Example 1 using the microorganisms *Stenotrophomonas maltophilia* and *Bacillus flexus* incubated in sugarcane juice.

Flavoured sweetener B (FS-B) was made in Example 2 using the microorganisms *Bacillus subtilis* and *Bacillus flexus* incubated in sugarcane juice.

Flavoured sweetener C (FS-C) was made in Example 3 using the microorganisms *Stenotrophomonas maltophilia* and *Bacillus flexus* incubated in diluted jaggery.

A flavoured sweetener was made in Example 4 using the microorganisms *Stenotrophomonas maltophilia* and *Bacillus flexus* incubated in a 1:1 mixture of sugarcane juice and sugarcane molasses.

Flavoured sweeteners were made in Example 5 using the microorganisms *Bacillus subtilis* and *Bacillus flexus* incubated with diluted sugarcane syrup.

A flavoured sweetener was made in Example 6 using the microorganism *Kluyveromyces* incubated with sugarcane juice.

A sweet sauce made from flavoured sweetener, salt water and optionally vinegar was made in Example 7. This process to make a sweet sauce uses the same process as Example 2, but adds an appropriate amount of salt water and optionally vinegar to the flavoured sweetener product.

Flavoured sweetener A sauce (FS-A sauce) was made in Example 8. This process to make a sweet sauce uses the same process as Example 1, but adds an appropriate amount of soy sauce during the cooking stage, and further cooks for approximately 1 hour at 80° C.

Reduced and increased sucrose flavoured sweeteners were made in Example 9. This process uses the same process as Example 2, but with an affination-like washing filtration process to separate the flavoured sweetener into reduced and increased sucrose fractions.

Flavour extracts of flavoured sweeteners, coconut sugars and sweet sauces were made in Example 10. The flavour extracts were prepared by solvent extraction and concentration.

Powdered and paste flavoured sweeteners and sweet sauces were made in Example 11. These powdered and paste products were prepared by mixing with starch or flour and optionally vegetable oil.

Food and beverage products with flavoured sweeteners were made in Example 12. These products include chocolate bars, hazelnut spreads, puddings, almond energy bars and ginger teas.

Food products with sweet sauce made from flavoured sweetener were made in Example 13. These products include spicy sweet sauce made with flavoured sweetener, onion sweet sauce made with flavoured sweetener, tempeh and green beans made with sweet sauce made with flavoured sweetener, air-fried sweet corn with sweet sauce made with flavoured sweetener and chicken stew made with powdered sweet sauce made with flavoured sweetener.

Organoleptic and Analytical Evaluation of the Flavoured Sweeteners

The basic quality characteristics of CNS is a reddish brown colour, microcrystalline texture and a sweet taste with flavours predominantly caramel and burnt. The caramel flavour is the characteristic flavour of molten raw sugar, and the burnt flavour is the characteristic flavour of burnt sugar.

The similarity of the flavoured sweetener to two high-quality traditional CNS (CNS-A and CNS-B) in terms of the basic quality characteristics were assessed by two methods: organoleptic evaluation and chemical analysis.

The organoleptic evaluation can be seen in Table 1 and encompasses colour, texture, sweet and salty taste assessment of the flavoured sweetener relative to traditional CNS. It is evident that the flavoured sweeteners were similar in colour, texture, sweetness and saltiness to the traditional products.

This organoleptic evaluation is complemented by the chemical analysis of sucrose, glucose, fructose, sodium and potassium in Table 2. The CNS-A contains approximately 70 wt % total sugars, while FS-A actually contains more with approximately 75 wt % total sugars. CNS-A and FS-A are both ranked 10 in saltiness, and have sodium contents of approximately 0.4 wt % and 0.1 wt % and potassium contents of approximately 0.6 wt % and 1.2 wt %, respectively.

The umami characteristic of a flavoured sweetener was also analysed by determining the concentration of glutamic acid (GA) and monosodium glutamate (MSG); inosine monophosphate (IMP) and disodium inosinate (DSI); and guanosine monophosphate (GMP) and disodium guanylate (DSG). It was found that the flavoured sweetener contains 0.09 wt % GA, 0.10 wt % MSG, as well as 0.11 wt % IMP and 0.13 wt % DSI, but no GMP nor DSG were detected at a level of 0.05 wt %. This is in contrast to CNS-A where none of the six compounds where detected at a level of 0.003 wt %. These umami molecules are potent flavour enhancers and therefore important for the organoleptic properties of the flavoured sweetener and food products derived from it.

Probably the umami molecules are generated from the metabolism of the microorganisms, rather than being present or generated from the raw material during heating. This is substantiated by the microorganisms when incubated exclusively on glucose or sucrose giving rise to an umami flavour.

The organoleptic evaluation of the presence of various flavour categories in CNS and the flavoured sweeteners can be seen in Table 3. The most important flavours are caramel followed by burnt and smoky. The flavoured sweeteners contain caramel and burnt flavours, as found in both CNS-A and CNS-B.

The organoleptic evaluation of flavour is supported by an aroma extract dilution analysis (AEDA) of the flavour molecules present in CNS-A, CNS-B and the flavoured sweeteners A to C. In the AEDA analysis a flavour extract is prepared and analysed as in Example 10. Due to the nature of the analysis, only volatile flavour molecules, i.e. aroma molecules, can be analysed, while non-volatile flavour molecules such as sugars and salts are not analysed. The flavour molecules in the flavour extract are separated by gas chromatography and identified by retention time, aroma characteristics, and in cases of doubt also by mass spectroscopy. A series of subsequent 1:1 dilutions are prepared and each dilution analysed. The highest number of dilutions in which a flavour molecule is detectable by smell is the flavour dilution (FD) number, which is a measure of the intensity of the flavour molecule in the aroma extract.

Figure 2:
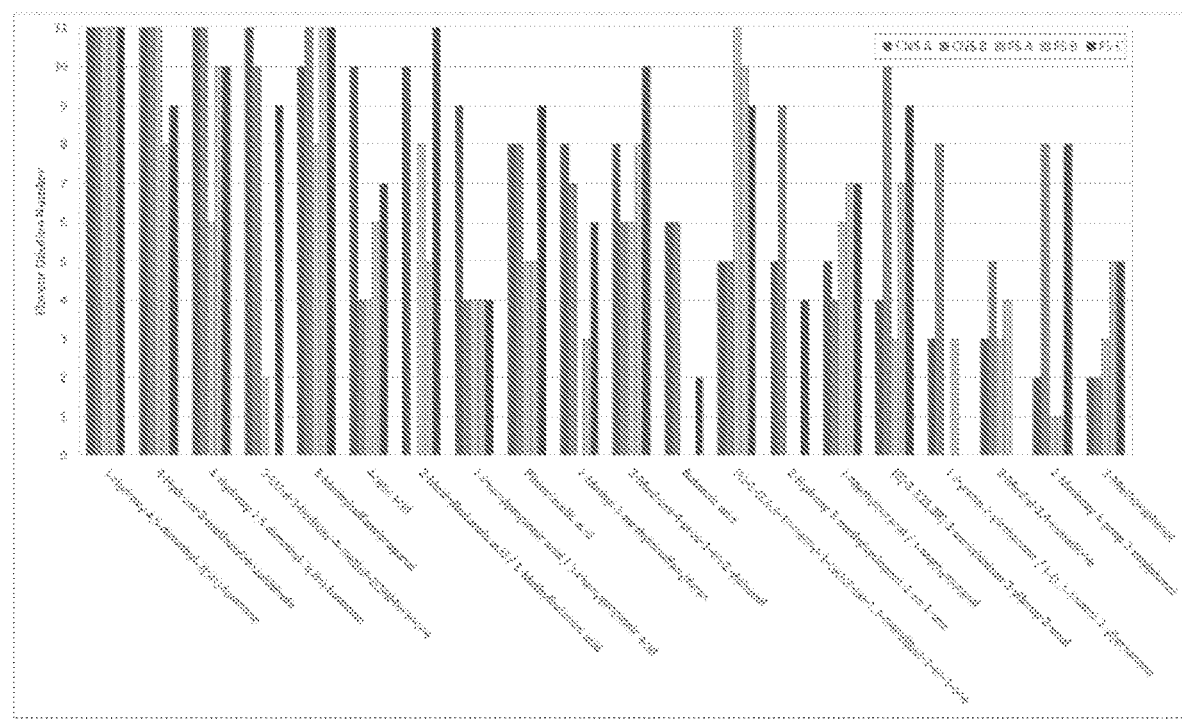
FIG. 2. Aroma Extract Dilution Analysis (AEDA) of CNS-A, CNS-B, flavoured sweetener A (FS-A; as made in Example 1), flavoured sweetener B (FS-B; as made in Example 2) and flavoured sweetener C (FS-C; as made in Example 3). The flavour (or aroma) extracts were prepared and analysed as described in Example 10. The flavour dilution (FD) number is the highest number of 1:1 dilutions where the flavour molecule can still be perceived at the sniffing port. The highest number of 1:1 dilutions performed was 11, and FD numbers higher than this cannot be specified.

In FIG. 2 the flavour molecules identified by AEDA as exhibiting Flavour Dilution (FD) numbers above 5 in at least one of CNS-A, CNS-B, FS-A, FSB, FS-C and FS-A sauce are identified, and listed along with their FD number and flavour categories.

In CNS-A and B the five flavour molecules present at the highest intensities are identical and are clearly linked to the flavour categories of CNS in Table 3. Therefore, the top five flavour molecules; 3-hydroxy-4,5-dimethyl-2(5-H)-furan-2-one, 4-hydroxy-3-methoxybenzaldehyde, 4-hydroxy-2,5-dimethyl-3(2H)-furanone, 5-ethyl-3-hydroxy-4-methyl-2(5H)-furanone and 3-methylsulfanylpropanal must contribute most of the common flavour characteristics of CNS. In contrast, CNS-A and CNS-B differ substantially in the remainder of the flavour molecules shown in Table 4. The fermented flavour present in CNS-A, but not CNS-B, is probably linked to the high FD number of certain acidic compounds, such as acetic acid, 2-methylbutanoic acid/3-methylbutanoic acid and 2-phenylpropionic acid/3-phenylpropionic acid which occur in CNS-A. CNS-A and CNS-B do have different nuances of flavour that are not reflected in Table 3, and these different nuances are most likely linked to the differences in flavour molecule composition in the bottom half of Table 4.

The flavoured sweetener A (FS-A; as in Example 1) has comparable FD numbers for 3-hydroxy-4,5-dimethyl-2(5H)-furan-2-one and 4-hydroxy-3-methoxybenzaldehyde, but is significantly lacking in 4-hydroxy-2,5-dimethyl-3(2H)-furanone and 5-ethyl-3-hydroxy-4-methyl-2(5H)-furanone. 4-Hydroxy-2,5-dimethyl-3(2H)-furanone and 5-ethyl-3-hydroxy-4-methyl-2(5H)-furanone are potent caramel flavour molecules, so their lower FD numbers indicate a lower intensity of caramel flavour in the FS-A. FS-B however contains 4-Hydroxy-2,5-dimethyl-3(2H)-furanone at FD number 10, indicating a better match to CNS. FS-C contains 4-Hydroxy-2,5-dimethyl-3(2H)-furanone at FD number 10 and 5-ethyl-3-hydroxy-4-methyl-2(5H)-furanone at FD number 9, thereby closely matching the top five flavour molecules present in CNS. The aroma characteristics of the flavoured sweeteners all have a large contribution from (E)-1-(2,6,6-trimethyl-1-cyclohexa-1,3-dienyl)but-2-en-1-one which is known to have a floral or apple-like flavour. The flavoured sweeteners contain several acidic flavour molecules, such as acetic acid and 2-Methylbutanoic acid/3-Methylbutanoic acid, which are present at higher intensities in CNS-A than CNS-B.

TABLE 1

Colour, texture and taste assessment of CNS-A, CNS-B, FS-A (Example 1), FS-B (Example 2) and FS-C (Example 3). Colour and texture were assessed visually, and texture also by mouthfeel of the products. CNS and flavoured sweeteners were tasted in 15 wt % dilution in tap water. First CNS-A was tasted, then the flavoured sweetener A, B or C, respectively. CNS-A was defined as having a rating of 10 in every category, and CNS-B, FS-A, FS-B and FS-C were ranked on this scale. The table contains the average rating reported by the three panellists, which all reported values within ±1 of the average.

| Product | Colour | Texture | Sweet | Salty |
|---|---|---|---|---|
| CNS-A | 10 | 10 | 10 | 10 |
| CNS-B | 9 | 10 | 10 | 10 |
| FS-A | 12 | 6 | 9 | 9 |
| FS-B | 11 | 6 | 8 | 9 |
| FS-C | 16 | 6 | 11 | 8 |

TABLE 2

The RDS, analysed sucrose, glucose, fructose, sodium and potassium contents and pH of CNS-A and FS-A (Example 1). The RDS was measured by a handheld refractometer (Atago, Japan) by diluting the sample 1:1 in distilled water and multiplying the reading by 2. The sugar assay was performed by high-performance liquid chromatography (HPLC) by an accredited laboratory. The pH was measured in a 1:1 dilution with distilled water by a handheld pH meter (Atago, Japan).

| Product | RDS (°Bx) | Sucrose (wt %) | Glucose (wt %) | Fructose (wt %) | Sodium (wt %) | Potassium (wt %) | pH |
|---|---|---|---|---|---|---|---|
| CNS-A | 90 | 63.2 | 3.1 | 3.5 | 0.424 | 0.606 | 5.5 |
| FS-A | 94 | 55.3 | 10.2 | 10.5 | 0.121 | 1.214 | 5.4 |

TABLE 3

Presence of principle flavours for CNS-A, CNS-B, FS-A (Example 1), FS-B (Example 2) and FS-C (Example 3) as reported by a taste panel consisting of three panellists. The caramel flavour is the flavour characteristic of molten raw sugar. The burnt flavour is the flavour characteristic of burnt sugar. The smoky flavour is the flavour characteristic of charcoal. The fermented flavour is the common flavour characteristic of soy sauce. The fruity flavour is the common flavour characteristic of fruits.

| Product | Caramel | Burnt | Smoky | Fermented | Fruity |
|---|---|---|---|---|---|
| CNS-A | Yes | Yes | Yes | Yes | No |
| CNS-B | Yes | Yes | Yes | No | No |
| FS-A | Yes | Yes | No | No | No |
| FS-B | Yes | Yes | No | No | No |
| FS-C | Yes | Yes | No | No | No |

TABLE 4

The 20 flavour molecules with the highest intensities were identified based on the criteria of having a FD number ≥ 6 in at least one of CNS-A, CNS-B, FS-A, FS-C, CNS sauce or FS-A sauce. The table contains the FD numbers for the The 20 flavour molecules with the highest intensities in CNS-A, CNS-B, FS-A (Example 1) and FS-C (Example 3).

| Flavour molecule | CNS-A | CNS-B | FS-A | FS-B | FS-C |
|---|---|---|---|---|---|
| 3-Hydroxy-4,5-dimethyl-2(5H)-furanone | ≥11 | ≥11 | ≥11 | ≥11 | ≥11 |
| 4-Hydroxy-3-methoxybenzaldehyde | ≥11 | ≥11 | ≥11 | 8 | 9 |
| 4-Hydroxy-2,5-dimethyl-3(2H)-furanone | ≥11 | ≥11 | 6 | 10 | 10 |
| 5-Ethyl-3-hydroxy-4-methyl-2(5H)-furanone | ≥11 | 10 | 2 | n.d. | 9 |
| 3-Methylsulfanylpropanal | 10 | ≥11 | 8 | ≥11 | ≥11 |
| Acetic acid | 10 | n.d. | 4 | 6 | 7 |
| 2-Methylbutanoic acid/3-methylbutanoic acid | 10 | n.d. | 8 | 5 | ≥11 |
| 2-Phenylpropionic acid/3-Phenylpropionic acid | 9 | 4 | 4 | 4 | 4 |
| Phenylacetic acid | 8 | 8 | 5 | 5 | 9 |
| 2-Methyl-3-methyldisulfanylfuran | 8 | 7 | n.d. | 3 | 6 |
| 2-Methoxy-4-prop-1-en-2-ylphenol | 8 | 6 | 6 | 8 | 10 |
| Butanoic acid | 6 | 6 | n.d. | 0 | 2 |
| (E)-1-(2,6,6-Trimethyl-1-cyclohexa-1,3-dienyl)but-2-en-1-one | 5 | 5 | ≥11 | 10 | 9 |
| 2-Hydroxy-3-methyl cyclopent-2-en-1-one | 5 | 9 | n.d. | 0 | 4 |
| 2-Methylbutanal/3-Methylbutanal | 5 | 4 | 6 | 7 | 7 |
| (E)-3-[(2S,3R)-3-Pentyl oxiran-2-yl]prop-2-enal | 4 | 10 | 3 | 7 | 9 |
| 1-Pyrazin-2-ylethanone/1-(1,3-thiazol-2-yl)ethanone | 3 | 8 | n.d. | 3 | n.d. |
| 2-methoxy-4-prop-2-enylphenol | 3 | 5 | 3 | 4 | n.d. |
| 2-Methoxy-4-prop-2-enylphenol | 2 | 8 | 1 | 1 | 8 |
| 2-Methoxyphenol | 2 | 2 | 3 | 5 | 5 | n.d. indicates that the flavour molecule was not detected.

Organoleptic and Analytical Evaluation of the Sweet Sauces

The basic quality characteristics of sweet sauce is a black glossy colour, a viscosity appropriate for use as a dipping sauce, a sweet, salty and umami taste with predominantly caramel and fermented flavour. The fermented flavour is the common flavour characteristic of soy sauce.

The similarity of the sweet sauces made from a flavoured sweetener to a coconut sugar derived sweet sauce (CNS sauce) in terms of their basic quality characteristics were assessed by two methods: organoleptic evaluation and chemical analysis.

The organoleptic evaluation can be seen in Table 5 and encompasses colour, texture, sweet and salty taste assessment of the sweet sauces made with flavoured sweeteners relative to a CNS sauce. It is evident that the sweet sauces made with flavoured sweeteners were similar in colour, texture, sweetness, saltiness and overall palatability to the CNS sauce.

The organoleptic evaluation of CNS sauce and FS-A sauce is supported by the chemical analysis of sucrose, glucose, fructose, sodium and potassium in Table 6. The CNS sauce contains approximately 60 wt % total sugars and the FS-A sauce approximately 55 wt % total sugars, and are both evaluated at a sweetness of 10.

The CNS sauce and FS-A sauce are given a saltiness rating of 10 and 11, respectively. Their sodium contents are approximately 1.5 wt % and 1.9 wt % and their potassium contents are approximately 0.4 wt % and 1.5 wt %, respectively. As for the CNS and flavoured sweeteners, it seems that the saltiness rating is mostly linked to the sodium content, and is fairly independent of the potassium content.

The organoleptic evaluation of the presence of various flavour categories in CNS sauce and the sweet sauces made from a flavoured sweetener can be seen in Table 7. The most important flavours are especially caramel, followed by burnt and fermented. The sweet sauces made from a flavoured sweetener have caramel and fermented flavours, as also found for the CNS sauce. FS-A sauce does not have the burnt and smoky flavours that the CNS sauce has.

Figure 3:
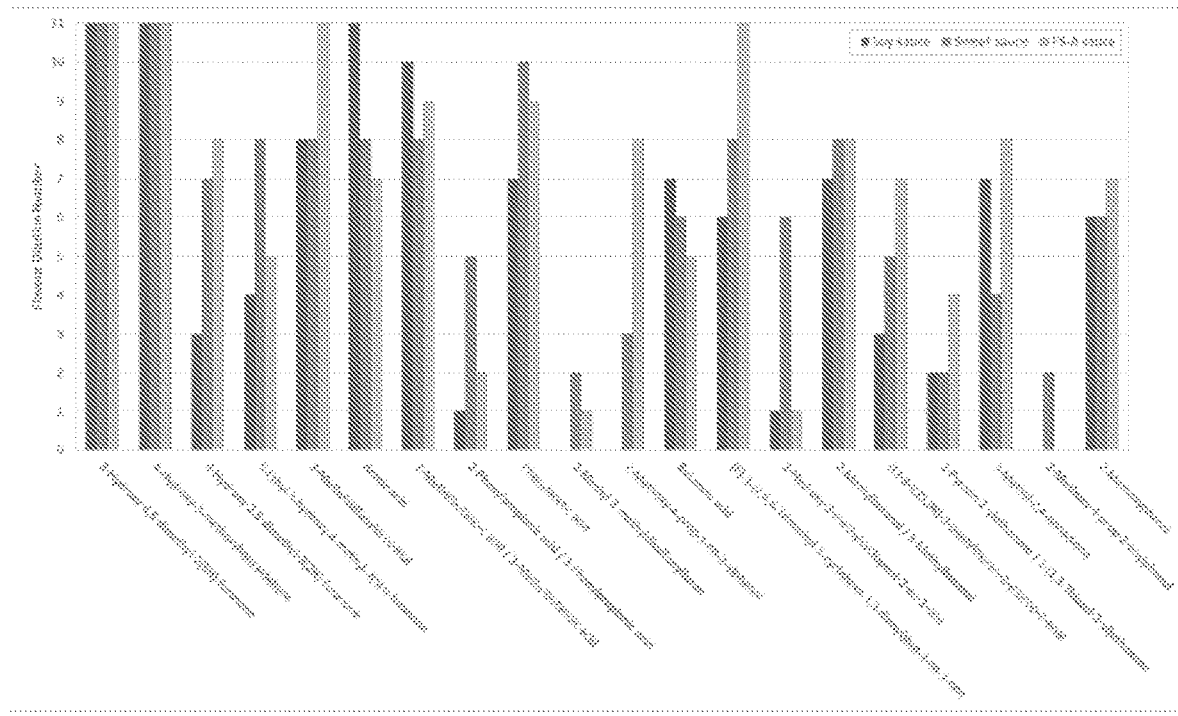
FIG. 3. Aroma Extract Dilution Analysis (AEDA) of commercial soy sauce, sweet sauce made from coconut sugar sauce (CNS sauce) and flavoured sweetener A sauce (FS-A sauce; as made in Example 8). The flavour (or aroma) extracts were prepared and analysed as described in Example 10. The flavour dilution (FD) number is the highest number of 1:1 dilutions were the flavour molecule can still be perceived at the sniffing port. The highest number of 1:1 dilutions performed was 11, and FD numbers higher than this cannot be specified.

The organoleptic evaluation of flavour is supported by an aroma extract dilution analysis (AEDA) of a soy sauce, CNS sauce and FS-A sauce. In FIG. 3 the flavour molecules identified by AEDA as exhibiting Flavour Dilution (FD) numbers above 5 in at least one of CNS-A, CNS-B, FS-A, FS-B, FS-C, CNS sauce and FS-A sauce are identified, and in Table 8 the flavour molecules are listed along with their FD number and flavour categories.

Of the ten most intense flavour molecules present in the sweet sauce made from CNS, seven are also found among the ten most intense flavour molecules present in CNS-A, thus confirming the important contribution that CNS makes in the flavour of sweet sauce.

The soy sauce analysed by AEDA is from the same manufacturer as the CNS sauce, and therefore likely the same or similar to the soy sauce used to manufacture the CNS sauce. This soy sauce was also used to make FS-A sauce in Example 8. This minimises the risk of differences in the soy sauce influencing the interpretation of the similarity between CNS sauce and FS-A sauce.

The FD numbers of the flavour molecules in the FS-A sauce generally match those of the CNS sauce closely. In fact, the only flavour molecules with a difference in FD number greater than 1 are 3-methylsulfanylpropanal, (E)-1-(2,6,6-trimethyl-1-cyclohexa-1,3-dienyl)but-2-en-1-one and 5-ethyl-3-hydroxy-4-methyl-2(5H)-furanone. The higher FD number of (E)-1-(2,6,6-trimethyl-1-cyclohexa-1,3-dienyl)but-2-en-1-one in the FS-A sauce is due to the large FD number of this compound in the FS-A, and vice versa the lower FD number of 5-ethyl-3-hydroxy-4-methyl-2(5H)-furanone is due to the low FD number in FS-A.

TABLE 5

Colour, texture and taste assessment of the coconut sugar derived sweet sauce (CNS sauce), sweet sauce made using flavoured sweetener-A (FS-A sauce; as in Example 8). Colour was assessed visually by smearing on a white piece of paper. Texture was assessed visually and by mouth feel of the products. The products were tasted neat, and before and after each tasting of a sweet sauce the CNS sauce was tasted. The CNS sweet sauce was defined as having a rating of 10 in every category, and the sweet sauce made with flavoured sweetener was ranked on this scale. The table contains the average rating reported by the three panellists, which all reported values within ±1 of the average.

| Product | Colour | Texture | Sweet | Salty |
|---|---|---|---|---|
| CNS sauce | 10 | 10 | 10 | 10 |
| FS-A sauce | 10 | 11 | 10 | 11 |

TABLE 6

The RDS, analysed sucrose, glucose, fructose, sodium and potassium contents and pH of soy sauce, coconut sugar sauce (CNS sauce), and flavoured sweetener A sauce (FS-A sauce; Example 8). The RDS was measured by a handheld refractometer (Atago, Japan) by diluting the sample 1:1 in distilled water and multiplying the reading by 2. The sugar assay was performed by high-performance liquid chromatography (HPLC) by an accredited laboratory. The pH was measured in a 1:1 dilution with distilled water by a handheld pH meter (Atago, Japan).

| Product | RDS (°Bx) | Sucrose (wt %) | Glucose (wt %) | Fructose (wt %) | Sodium (wt %) | Potassium (wt %) | pH |
|---|---|---|---|---|---|---|---|
| Soy sauce | 48 | 0.2 | 10.0 | 10.4 | 5.806 | 0.168 | 3.2 |
| CNS sauce | 79 | 32.7 | 13.5 | 12.5 | 1.515 | 0.394 | 4.7 |
| FS-A sauce | 82 | 31.8 | 11.5 | 12.4 | 1.858 | 1.465 | 4.8 |

TABLE 7

Presence of principal flavours for coconut sugar sauce (CNS sauce) and sweet sauce made using flavoured sweetener-A (FS-A sauce; as in Example 8) as reported by a taste panel consisting of three panellists. The caramel flavour is the flavour characteristic of molten raw sugar. The burnt flavour is the flavour characteristic of burnt sugar. The smoky flavour is the flavour characteristic of charcoal. The fermented flavour is the common flavour characteristic of soy sauce. The fruity flavour is the common flavour characteristic of fruits.

| Product | Caramel | Burnt | Smoky | Fermented | Fruity |
|---|---|---|---|---|---|
| CNS sauce | Yes | Yes | Yes | Yes | Yes |
| FS-A sauce | Yes | No | No | Yes | No |

TABLE 8

The 20 flavour molecules with the highest intensities were identified based on the criteria of having a FD number ≥ 6 in at least one of CNS-A, CNS-B, FS-A, FS-C, CNS sauce or FS-A sauce. The table contains the FD numbers for the 20 flavour molecules with the highest intensities in soy sauce, sweet sauce and FS-A sauce (Example 8). These were found to be identical to those present in the above samples of CNS and flavoured sweeteners.

| | FD Number | | |
|---|---|---|---|
| Flavour molecule | Soy sauce | CNS sauce | FS-A sauce |
| 3-Hydroxy-4,5-dimethyl-2(5H)-furanone | ≥11 | ≥11 | ≥11 |
| 4-Hydroxy-3-methoxybenzaldehyde | ≥11 | ≥11 | ≥11 |
| 4-Hydroxy-2,5-dimethyl-3(2H)-furanone | 3 | 7 | 8 |
| 5-Ethyl-3-hydroxy-4-methyl-2(5H)-furanone | 4 | 8 | 5 |
| 3-Methylsulfanylpropanal | 8 | 8 | ≥11 |
| Acetic acid | ≥11 | 8 | 7 |
| 2-Methylbutanoic acid/3-Methylbutanoic acid | 10 | 8 | 9 |
| 2-Phenylpropionic acid/3-Phenylpropionic acid | 1 | 5 | 2 |
| Phenylacetic acid | 7 | 10 | 9 |
| 2-Methyl-3-methyldisulfanylfuran | n.d. | 2 | 1 |
| 2-Methoxy-4-prop-1-en-2-ylphenol | n.d. | 3 | 8 |
| Butanoic acid | 7 | 6 | 5 |
| (E)-1-(2,6,6-Trimethyl-1-cyclohexa-1,3-dienyl)but-2-en-1-one | 6 | 8 | ≥11 |
| 2-Hydroxy-3-methylcyclopent-2-en-1-one | 1 | 6 | 1 |
| 2-Methylbutanal/3-Methylbutanal | 7 | 8 | 8 |
| (E)-3-[(2S,3R)-3-pentyloxiran-2-yl]prop-2-enal | 3 | 5 | 7 |
| 1-Pyrazin-2-ylethanone/1-(1,3-Thiazol-2-yl)ethanone | 2 | 2 | 4 |
| 2-methoxy-4-prop-2-enylphenol | 7 | 4 | 8 |
| 2-Methoxy-4-prop-2-enylphenol | 0 | 2 | n.d. |
| 2-Methoxyphenol | 6 | 6 | 7 | n.d. indicates that the flavour molecule was not detected.

Distinguishing Characteristics of the Flavoured Sweeteners and Sauces

The previous sections dealt with the similarity in taste and flavour of the flavoured sweetener to coconut sugar and flavoured sauce to sweet sauce. This section instead deals with unique and distinguishing features of the flavoured sweetener and flavoured sauces.

The fundamental difference between the flavoured sweetener and coconut sugar is the raw material and the use of selected microorganisms to modify it. The raw material for the flavoured sweetener is an unrefined plant extract containing sucrose as the main solute, especially a sugarcane extract. Coconut sugar on the other hand is made from coconut inflorescence sap, and palm sugar from an extract from palm species such as the Palmyra palm, date palm, sugar date palm, arenga palm and nipa palm.

These palm species have in common that they all fixate carbon dioxide by the $C_3$ metabolic pathway, this causes all their carbon containing molecules to be relatively depleted in $^{13}C$ relative to plants that fixate carbon dioxide by the $C_4$ mechanism, such as sugarcane. $C_3$ plants have carbon-13 to carbon-12 isotope ratios ($^{13}C/^{12}C$) of less than or equal to 11 parts per thousand, while $C_4$ plants have $^{13}C/^{12}C$ of more than or equal to 11 parts per thousand. A third mechanism of carbon dioxide fixation is known as Crassulacean acid metabolism (CAM), which overlap with $C_4$ plants in their $^{13}C/^{12}C$ range of approximately 11.09 to 11.11 parts per thousand.

An alternative way of denoting the differences in carbon-13 and carbon-12 is by the isotopic signature delta carbon-13 ($\delta^{13}C$), which is defined relative to the material Pee Dee Belemnite (PDB) as:

$$\delta^{13}C = \left(\frac{(^{13}C/^{12}C)_{sample}}{(^{13}C/^{12}C)_{PDB}} - 1\right) * 1000\%_0$$

PDB has a characteristically high $^{13}C$ content and by the definition above has $\delta^{13}C=0$. As all plants are relatively depleted in $^{13}C$ compared to PDB they have negative $\delta^{13}C$ values. The $^{13}C$ of $C_4$ plants is in the range of −5‰ to −20‰, for CAM plants −11‰ to −13.5‰ and for $C_3$ plants −20‰ to −40‰. Some examples of $C_3$, $C_4$ and CAM plants and their $^{13}C/^{12}C$ and $\delta^{13}C$ are given in Table 9.

TABLE 9

The carbon dioxide fixation pathway, carbon-13 to carbon-12 ratio ($^{13}C/^{12}C$) and carbon isotopic signature relatively to Pee Dee Belemnite ($\delta^{13}C$) of various sucrose-producing plants.[1,2]

| Plant species | $CO_2$ fixation pathway | $^{13}C/^{12}C$ (‰) | $\delta^{13}C$ (‰) |
|---|---|---|---|
| Sugar beet | $C_3$ | 10.90 | −30 |
| Coconut palm | $C_3$ | 10.97 | −24 |
| Sorghum | $C_4$ | 11.07 | −14.5 |
| Maize | $C_4$ | 11.08 | −14 |
| Agave | CAM | 11.09 | −13 |
| Sugarcane | $C_4$ | 11.10 | −12 |

[1]Smith, B. N. & Epstein, S., 1971, 'Two categories of $^{13}C/^{12}C$ ratios for higher plants' *Plant Physiol.*, Vol. 47, pp. 380-384.
[2]Sage, R. F. & Zhu, X.-G., 2011, 'Exploiting the engine of $C_4$ photosynthesis' *Experimental Botany*, vol. 62, pp. 2989-3000.

Another way to distinguish the flavoured sweetener made from a sugarcane raw material is the presence of aconitic acid, which occurs in sugarcane juice, and therefore the flavoured sweetener, at more than 0.1 wt %. Also, the flavoured sweetener has a high ratio of potassium to sodium (K/Na) that can be calculated from the data in Table 2. CNS-A has a K/Na of 1.4 while FS-A has a K/Na of 10.

Due to the metabolism of the microorganisms, the flavoured sweetener contains appreciable amounts of glutamic acid (GA) and monosodium glutamate (MSG), and also nucleoside monophosphates such as inosine monophosphate (IMP), disodium inosinate (DSI), guanosine monophosphate (GMP) and disodium guanylate (DSG). The sum of GA and MSG is determined to be 0.19 wt %, and the sum of IMP, DSI, GMP and DSG occurs is determined to be at least 0.24 wt %, of which IMP and DSI appear to make up the bulk. None of these compounds were detected in CNS at a level of 0.003 wt %.

Moreover, as the flavoured sweetener has not been stabilised against microbial growth by addition of sodium sulphite, it will contain less than 5 mM of sulphite ions.

EXAMPLES

Example 1. Method to Make Flavoured Sweetener Using Sugarcane Juice Incubated with the *Stenotrophomonas maltophilia* and *Bacillus flexus*

Raw Material

The unrefined plant extract containing sucrose as the main solute was crude sugarcane juice. The crude sugarcane juice was produced by crushing sugarcane (*Saccharum officinarum*) through the rollers of a table-top sugarcane juicer machine to produce sugarcane juice with a pH of 5.2 and a refractory dry substance content of around 12° Bx. 1 kg of this unrefined plant extract containing sucrose as the main solute was coarsely filtered with a muslin cloth such as fabrique and pasteurized in a metal vessel heated by an electrical hotplate (Heidolph, Germany) at 70° C. to 72° C. for 2 min with occasional stirring with a stainless steel spoon.

1 kg of the raw material was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bio-block', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of while agitating the bioreactor at 400 rpm until the DO sensor value had stabilised at 100%.

Inoculum

Individual overnight cultures of strains, *Stenotrophomonas maltophilia* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Figure 4:
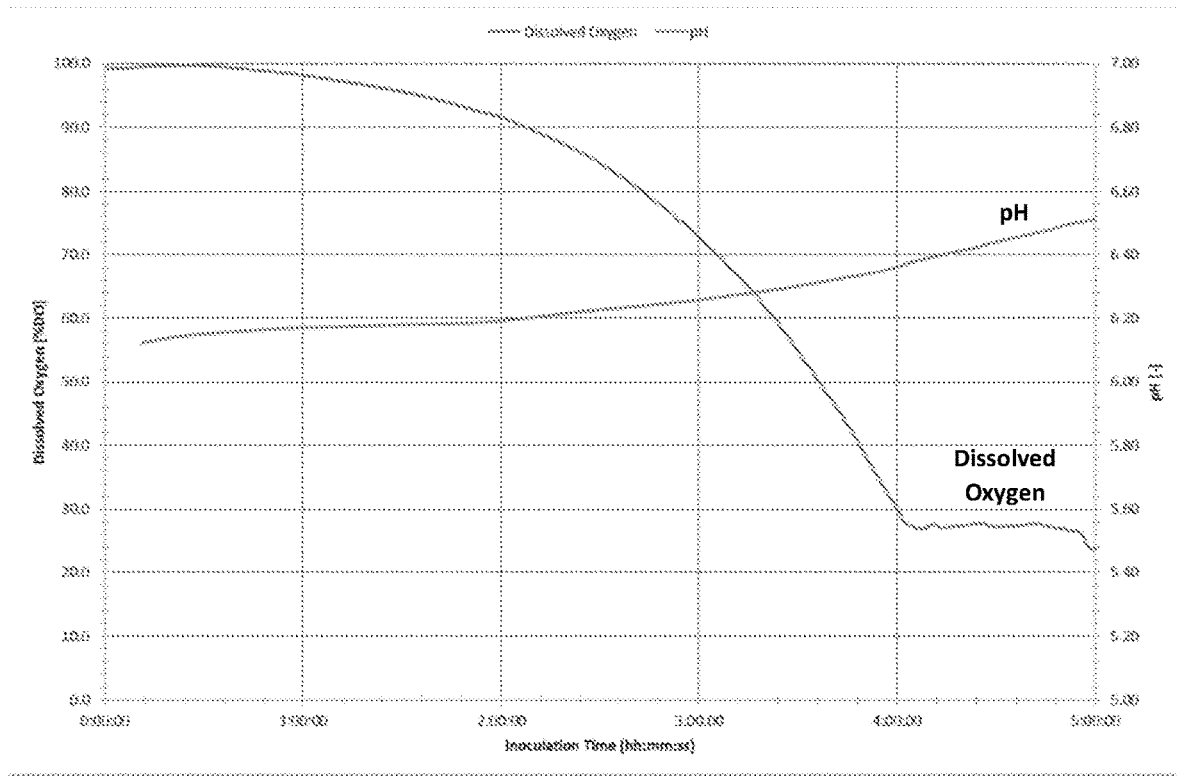
FIG. 4. Time profile of DO and pH using *Stenotrophomonas maltophilia*, and *Bacillus flexus*, as in Example 1. The Dissolved Oxygen (DO) was measured by an optical oxygen sensor (Hamilton, U.S.A.). 100% DO represents the saturation limit of $O_2$ in the media when gassing with air and was calibrated before inoculation. DO was controlled to be minimum 30% during the incubation by an oxygen cascade. pH was measured by an Ag/AgCl glass electrode (Mettler Toledo, Switzerland). The incubation medium was crude sugarcane juice and the inoculation volume was 0.5% of each strain grown in Tryptic Soy Broth (TSB; Oxoid, U.K.) at an Optical Density (OD) of 1. No other nutrients were added in the incubation.

Incubation pH was adjusted prior to and during incubation to be constant at 6.0. The adjustment was carried out with addition of an appropriate amount of 2 M Na2CO3 via the multi-incubator base pump system. Incubation was initiated by the addition into the bioreactor of a 0.5% by volume inoculum scaled by the inverse of the measured OD at 600 nm of each inoculum: i.e. OD=1 gives an inoculation volume of 5 mL, while OD=0.5 gives an inoculation volume of 10 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm. The incubation was carried out at 33° C. for 5 hours monitoring pH and DO. The time profile of the DO and pH can be seen in FIG. 4. After 5 hours the incubation was stopped.

Cooking

The modified unrefined plant extract was transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a warm, brown, caramel-like aroma and dark brown colour development was detected. When the process temperature reached approximately 120° C. the bowl was taken off the hotplate and stirred vigorously for 3 minutes. During these 3 minutes the syrup became more viscous until becoming a solid amorphous product.

The colour, texture and basic taste assessment of the flavoured sweetener (FS-A) can be seen in Table 1, the RDS, sucrose, glucose, fructose, sodium and potassium contents and pH in Table 2, the flavour categories in Table 3 and finally the most prominent flavour molecules in Table 4.

Example 2. Method to Make Flavoured Sweetener Using Sugarcane Juice Incubated with *Bacillus subtilis* and *Bacillus flexus* and an Incubation Time of 2, 3, 4 or 5 Hours Raw Material The unrefined plant extract containing sucrose as the main solute was crude sugarcane juice. The crude sugarcane juice was produced by crushing sugarcane (*Saccharum officinarum*) through the rollers of a table-top sugarcane juicer machine to produce sugarcane juice with a pH of 5.3 and a refractory dry substance content of around 13° Bx. 1 kg of this unrefined plant extract containing sucrose as the main solute was coarsely filtered with a muslin cloth such as fabrique and pasteurized in a metal vessel heated by an electrical hotplate (Heidolph, Germany) at 70° C. to 72° C. for 2 min with occasional stirring with a stainless steel spoon.

1 kg of the raw material was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bio-block', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of 0.1 vvm while agitating the bioreactor at 400 rpm until the DO sensor value had stabilised at 100%.

Inoculum

Individual overnight cultures of strains *Bacillus subtilis* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Incubation pH was adjusted prior to incubation to 6.0. The adjustment was carried out with addition of an appropriate amount of 2 M Na2CO3 from a sterile syringe through an inlet port. Incubation was initiated by the addition into the bioreactor of a 0.5% by volume inoculum scaled by the inverse of the measured OD at 600 nm of each inoculum: i.e. OD=1 gives an inoculation volume of 5 mL, while OD=0.5 gives an inoculation volume of 10 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm. Four different incubations were performed simultaneously and carried out at 33° C. for 2, 3, 4, and 5 hours monitoring pH and DO. After 2, 3, 4, 5 hours, respectively, a 1 mL sample of the modified unrefined plant extract was taken through an inlet port with a sterile syringe and the incubation stopped. The 1 mL sample of modified unrefined plant extract was used to evaluate the microbiology of the incubation.

Microbiology

The CFU/mL of the strains *Bacillus subtilis* and *Bacillus flexus* were enumerated by using spread plating technique. For the dilution series sterile CMO 129 tryptic soy broth (TSB) (Oxoid, U.K.) was used. 0.1 mL dilution was transferred on CMO 131 tryptic soy agar (TSA) (Oxoid, U.K.) and spread with L-shaped spreader in circular motion on the surface of TSA. The samples were done in duplicates. The plates were incubated at 33° C. for 24 hr and enumerated thereafter. The results are presented in the text of the Detailed Description.

Cooking

Each of the modified unrefined plant extracts containing sucrose as the main solute was transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a warm, brown, caramel-like aroma and dark brown colour development was detected. When the process temperature reached approximately 120° C. the bowl was taken off the hotplate and stirred vigorously for 3 minutes. During these 3 minutes the syrup became more viscous until becoming a solid amorphous product, except the product incubated for 5 hours, which became a solid microcrystalline product.

The basic taste assessment and flavour categories of the flavoured sweetener products at different incubation times were assessed by a taste panel consisting of three panelist.

The best product was determined to be the one incubated for 4 hours, which is denoted flavoured sweetener B (FS-B) in the text. The colour, texture and basic taste assessment of FS-B can be seen in Table 1, the flavour categories in Table 3, and finally the most prominent flavour molecules in Table 4.

Example 3. Method to Make Flavoured Sweetener Using Jaggery Incubated with *Bacillus subtilis* and *Bacillus flexus*

Raw Material

The unrefined plant extract containing sucrose as the main solute was sugarcane jaggery. The sugarcane jaggery was a commercial product and was diluted with boiling water to a refractory dry substance content of around 12° Bx. 1 kg of this raw material was coarsely filtered with a muslin cloth such as fabrique and pasteurized in a metal vessel heated by an electrical hotplate (Heidolph, Germany) at 70° C. to 72° C. for 2 min with occasional stirring with a stainless steel spoon.

1 kg of the raw material was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bio-block', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of 0.1 vvm while agitating the bioreactor at 400 rpm until the DO sensor value had stabilised at 100%.

Inoculum

Individual overnight cultures of strains, *Stenotrophomonas maltophilia* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Incubation pH was adjusted prior to and during incubation to be constant at 6.0. The adjustment was carried out with addition of an appropriate amount of 2 M Na2CO3 via the multi-incubator base pump system. Incubation was initiated by the addition into the bioreactor of a 0.5% by volume inoculum scaled by the inverse of the measured OD at 600 nm of each inoculum: i.e. OD=1 gives an inoculation volume of 5 mL, while OD=0.5 gives an inoculation volume of 10 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm. The incubation was carried out at 33° C. for 5 hours monitoring pH and DO. After 5 hours the incubation was stopped.

Cooking

The modified unrefined plant extract was transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a warm, brown, caramel-like aroma and dark brown colour development was detected. When the process temperature reached approximately 120° C. the bowl was taken off the hotplate and stirred vigorously for 3 minutes. During these 3 minutes the syrup became more viscous until becoming a solid amorphous product.

The colour, texture and basic taste assessment of the flavoured sweetener (FS-C) can be seen in Table 1, the flavour categories in Table 3 and finally the most prominent flavour molecules in Table 4.

Example 4. Method to Make Flavoured Sweetener Using Sugarcane Juice and Sugarcane Molasses Incubated with *Stenotrophomonas maltophilia* and *Bacillus flexus*

Raw Material

The unrefined plant extract containing sucrose as the main solute was crude sugarcane juice mixed with sugarcane molasses. The crude sugarcane juice was produced by crushing sugarcane (*Saccharum officinarum*) through the rollers of a table-top sugarcane juicer machine to produce sugarcane juice with a pH of 5.2 and a refractory dry substance content of around 11° Bx. The sugarcane molasses was obtained as a commercial product and was diluted to 13° Bx with boiling water and the mixed 1:1 with the crude sugarcane juice. 1 kg of this raw material was coarsely filtered with a muslin cloth such as fabrique and pasteurized in a metal vessel heated by an electrical hotplate (Heidolph, Germany) at 70° C. to 72° C. for 2 min with occasional stirring with a stainless steel spoon.

1 kg of the raw material was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bio-block', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of 0.1 vvm while agitating the bioreactor at 400 rpm until the DO sensor value had stabilised at 100%.

Inoculum

Individual overnight cultures of strains, *Stenotrophomonas maltophilia* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Incubation pH was adjusted prior to and during incubation to be constant at 6.0. The adjustment was carried out with addition of an appropriate amount of 2 M Na2CO3 via the multi-incubator base pump system. Incubation was initiated by the addition into the bioreactor of a 0.5% by volume inoculum scaled by the inverse of the measured OD at 600 nm of each inoculum: i.e. OD=1 gives an inoculation volume of 5 mL, while OD=0.5 gives an inoculation volume of 10 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm. The incubation was carried out at 33° C. for 5 hours monitoring pH and DO. After 5 hours the incubation was stopped.

Cooking

The modified unrefined plant extract was transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a warm, brown, caramel-like aroma and dark brown colour development was detected. When the process temperature reached approximately 120° C. the bowl was taken off the hotplate and stirred vigorously for 3 minutes. During these 3 minutes the syrup became more viscous until becoming a solid amorphous product.

Example 5. Method to Make Flavoured Sweetener Using Sugarcane Syrup Diluted 1:1, 1:2, 1:3 and 1:4 in Water Incubated with *Bacillus subtilis* and *Bacillus flexus*

Raw Material

The unrefined plant extract containing sucrose as the main solute was a sugarcane syrup. The sugarcane syrup was obtained from a sugarcane mill in Brazil, and was produced from sugarcane juice by clarifying and boiling to produce a sugarcane syrup with a pH of 6.0 and a refractory dry substance (RDS) content of around 60° Bx. Four different concentrations of sugarcane syrup were prepared by dilution 1:4, 1:3, 1:2 and 1:1 with boiling water, having an RDS of 12° Bx, 16° Bx, 22° Bx and 30° Bx, respectively. 1 kg each of these unrefined plant extracts containing sucrose as the main solute were coarsely filtered with a muslin cloth such as fabrique and pasteurized in a metal vessel heated by an electrical hotplate (Heidolph, Germany) at 70° C. to 72° C. for 2 min with occasional stirring with a stainless steel spoon.

1 kg each of the raw materials was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bioblock', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of 0.1 vvm while agitating the bioreactor at 400 rpm until the DO sensor value had stabilised at 100%.

Inoculum

Individual overnight cultures of strains *Bacillus subtilis* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Figure 5:
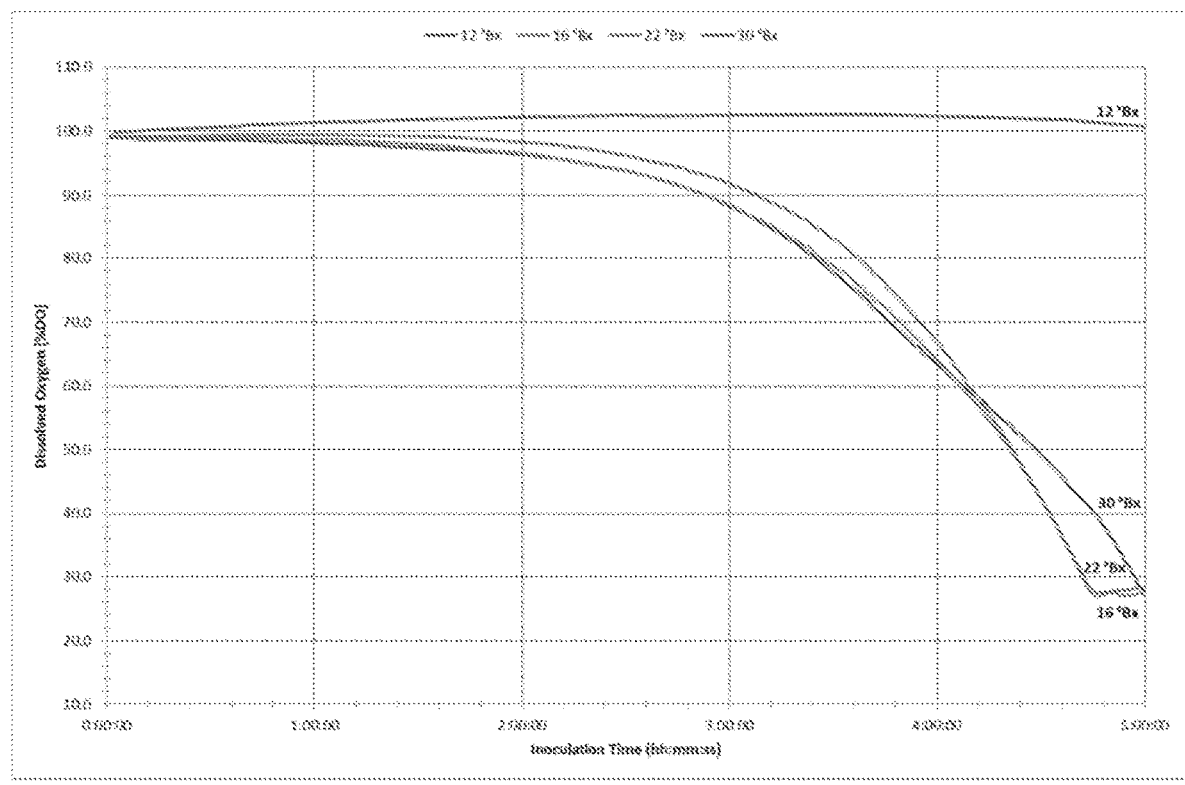
FIG. 5. Time profile of DO and pH using *Bacillus subtilis*, and *Bacillus flexus*, as in Example 5. The parameters and equipment used are the same as in FIG. 4, except that the incubation medium was diluted sugarcane syrup. Each line in the time profile is the DO curve for one of four simultaneous incubations done under identical conditions, with the one exception being the concentration of the sugarcane syrup of 12° Bx, 16° Bx, 22° Bx and 30° Bx, respectively.

Incubation pH was not adjusted prior to or during the incubation, but remained within 5.8 to 6.2 throughout for all four incubations. Incubation was initiated by the addition into the bioreactor of a 0.5% by volume inoculum scaled by the inverse of the measured OD at 600 nm of each inoculum: i.e. OD=1 gives an inoculation volume of 5 mL, while OD=0.5 gives an inoculation volume of 10 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm. Four different incubations were performed simultaneously in the 12° Bx, 16° Bx, 22° Bx and 30° Bx raw materials, respectively, and carried at 33° C. for 5 hours monitoring pH and DO. The time profile of the DO can be seen in FIG. 5 for each incubation.

Cooking

Each of the modified unrefined plant extracts containing sucrose as the main solute was transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a warm, brown, caramel-like aroma and dark brown colour development was detected. When the process temperature reached approximately 120° C. the bowl was taken off the hotplate and stirred vigorously for 3 minutes. During these 3 minutes the syrup became more viscous, and then grew lighter in colour and opaque, until becoming a solid semi-crystalline product.

Example 6. Method to Make Flavoured Sweetener Using Sugarcane Juice Incubated with a *Kluyveromyces* Species and an Incubation Temperature of 20° C., 33° C. and 40° C. and pH of 5 or 7

Raw Material

The unrefined plant extract containing sucrose as the main solute was crude sugarcane juice. The crude sugarcane juice was produced by crushing sugarcane (*Saccharum officinarum*) through the rollers of a table-top sugarcane juicer machine to produce sugarcane juice with a pH of 5.3 and a refractory dry substance content of around 13° Bx. 1 kg of this unrefined plant extract containing sucrose as the main solute was coarsely filtered with a muslin cloth such as fabrique and pasteurized in a metal vessel heated by an electrical hotplate (Heidolph, Germany) at 70° C. to 72° C. for 2 min with occasional stirring with a stainless steel spoon.

1 kg of the raw material was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bioblock', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of 0.1 vvm while agitating the bioreactor at 400 rpm until the DO sensor value had stabilised at 100%.

Inoculum

Individual overnight cultures of strains, *Stenotrophomonas maltophilia* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Incubation

Four different incubations were performed simultaneously, without pH adjustment (i.e. a pH of approximately 5) at incubation temperatures of 20° C., 33° C. and 40° C., respectively. The fourth incubation was also performed at an incubation temperature of 40° C. with pH adjusted prior to and during incubation to be constant at approximately pH 7.

Figure 6:
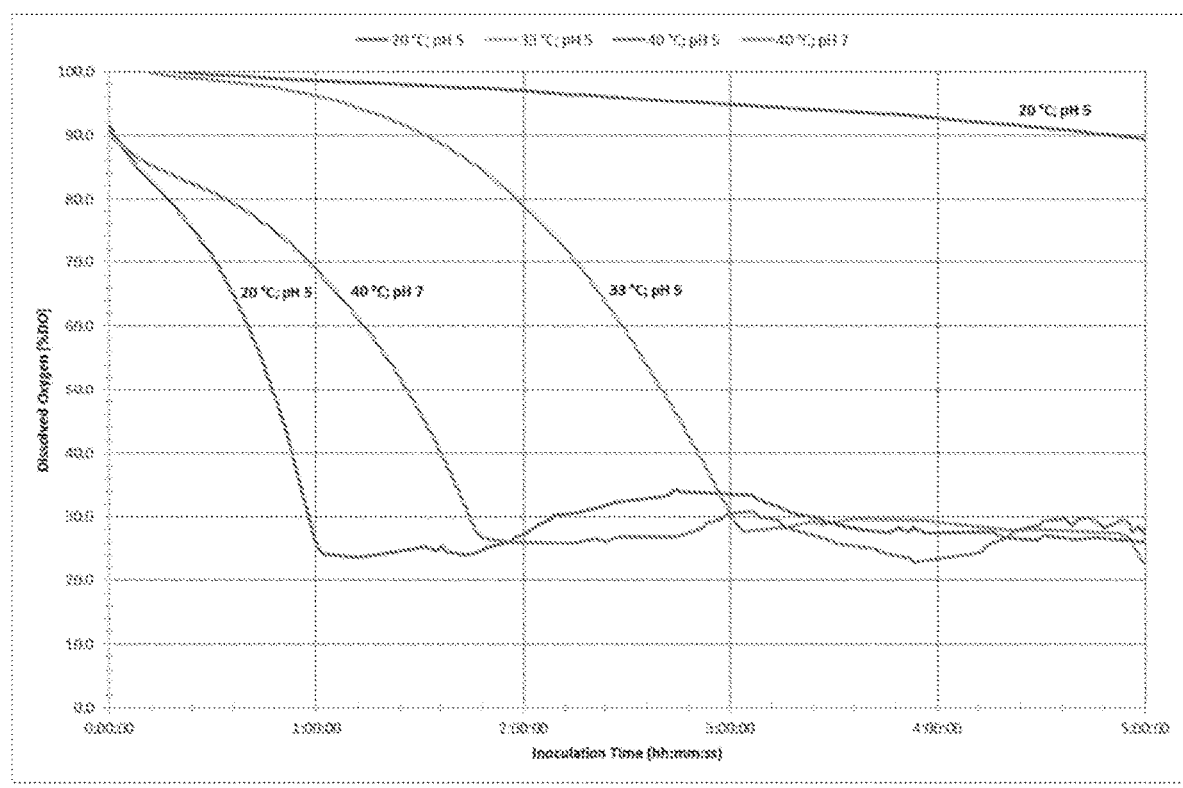
FIG. 6. Time profile of DO and pH using a *Kluyveromyces* species, as in Example 6. The parameters and equipment used are the same as in FIG. 4. Each line in the time profile is the DO curve for one of four simultaneous incubations done under identical conditions, with the one exception being the incubation temperature and pH of 20° C. & pH 5; 33° C. & pH 5; 40° C. & pH 5 and 30° Bx & pH 7, respectively.

The adjustment was carried out with addition of an appropriate amount of 2 M Na2CO3 via the multi-incubator base pump system. Incubation was initiated by the addition into the bioreactor of a 1% by volume inoculum scaled by the inverse of the measured OD at 600 nm of the inoculum: i.e. OD=1 gives an inoculation volume of 10 mL, while OD=0.5 gives an inoculation volume of 20 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm. The incubation was carried out for 5 hours monitoring pH and DO. The time profile of the DO can be seen in FIG. 6. After 5 hours the incubation was stopped.

Cooking

Each of the modified unrefined plant extracts were transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a warm, brown, caramel-like aroma and dark brown colour development was detected. When the process temperature reached approximately 120° C. the bowl was taken off the hotplate and stirred vigorously for 3 minutes. During these 3 minutes the syrup became more viscous until becoming a solid amorphous product.

Example 7. Process to Make Sweet Sauce from Flavoured Sweetener, Salt Water and Optionally Vinegar The sweet sauce was prepared from the flavoured sweetener in Example 2 which was incubated for 5 hours. 40 g of flavoured sweetener was dissolved in 20 g of de-ionised (DI) water. The mixture was cooked on an electrical hotplate (Heidolph, Germany) with occasional stirring. The cooking time was around 45 minutes and the sweet sauce yield was 50 g. To this sauce 2 g of sodium chloride was added. The sauce was dark brown with an RDS of 67° Bx.

The taste of the sweet sauce was sweet and salty, and it contained caramel and burnt flavours. However, it did not contain the fermented flavour. The fermented flavour could be instilled in the sweet sauce by addition of approximately 1 to 5 wt. % vinegar or acetic acid.

Example 8. Process to Make Sauce from a Flavoured Sweetener and Soy Sauce

The process was carried out as in Example 1, but the process flow was changed when the flavoured sweetener reached 120° C. At this point, the flavoured sweetener is cooled to about 80° C. and weighs about 146 g. 52 g of soy sauce and 50 g of tap water was added. The mixture was cooked on an electrical hotplate (Heidolph, Germany) with occasional stirring. The cooking time was around 45 minutes and the final sweet sauce yield was 196 g.

The colour, texture and basic taste assessment of the sweet sauce product can be seen in Table 5, the RDS, sucrose, glucose, fructose, sodium and potassium contents and pH in Table 6, the flavour categories in Table 7 and finally the most prominent flavour molecules in Table 8.

Example 9. Process to Make Reduced and Increased Sucrose Flavoured Sweeteners Reduced sucrose and increased sucrose flavoured sweeteners were prepared from the flavoured sweetener in Example 2 which was incubated for 5 hours. This flavoured sweetener was chosen because a semi-crystalline flavoured sweetener is needed for the method.

5 g flavoured sweetener was ground and washed with 2.5 g of a mixture of 70 wt. % ethanol and 30 wt. % water (70% ethanol) during suction filtration using a Büchner funnel. This treatment allows washing off part of the coating of the sucrose crystals and transferring it to the filtrate, thereby making a reduced sucrose flavoured sweetener on the filtrate side, while leaving an increased sucrose flavoured sweetener on the residue side.

The reduced sucrose nature of the filtrate was confirmed by analysing the filtrate. The filtrated liquid was evaporated on a rotary evaporator at 80° C., yielding 0.73 g of reduced sucrose flavoured sweetener. The dried filtrate was dissolved 1:1 in distilled water. The refractometric dry substance (RDS) of the solution was measured by handheld refractometer (Atago, Japan) to be 14° Bx, and the pH to be 5.4 by handheld pH meter (Atago, Japan).

In contrast, the RDS of a 1:1 solution in distilled water of the flavoured sweetener prior to washing is 20° Bx and the pH 5.0. This indicates that the dried filtrate has a reduced sucrose concentration, and therefore that the retentate has an increased sucrose concentration compared to the flavoured sweetener prior to washing.

Example 10. Process to Make Flavour Extracts from Flavoured Sweeteners, Coconut Sugars and Sweet Sauces Flavour extracts were prepared from CNS-A, CNS-B, flavoured sweetener A (FS-A; as made in Example 1), flavoured sweetener B (FS-B; as made in Example 2) and flavoured sweetener C (FS-C; as made in Example 3), coconut sugar sauce (CNS sauce) and flavoured sweetener A sauce (FS-A sauce; as made in Example 8).

Each flavour extract was prepared from 50 g of CNS, FS, CNS sauce or FS sauce dissolved in distilled water and extracted with 100 mL diethyl ether. The organic layer was separated and the flavour molecules concentrated by Solvent Assisted Flavour Evaporation (SAFE) distillation yielding a flavour extract.

The flavour extracts were analysed by aroma extract dilution analysis (AEDA) and therefore dried over sodium sulphate and concentrated to 100 µL using a vigreux column. The concentrated flavour extract (100 µL) was diluted stepwise with solvent in a 1:1 ratio. Each dilution was separated by a Trace gas chromatograph (Finnigan, Germany) with a 30 m long, 0.25 mm inner diameter and 0.25 µm film thickness Free Fatty Acid & Phenols column (FFAP; J&W Scientific) with a helium flow rate of 1.5 mL/min. Detection was by flame ionisation (in hydrogen and synthetic air) and olfactometry with a specialist. The Flavour Dilution (FD) number is the highest number of 1:1 dilutions were the flavour molecule can still be perceived at the sniffing port. The highest number of 1:1 dilutions performed was 11, and FD numbers higher than this cannot be specified. The identity of flavour molecules is determined primarily by retention index and odour characteristics, but in some cases also Gas Chromatography-Mass Spectroscopy (GC-MS) all relative to pure flavour molecule standards.

Due to the nature of the extraction and the olfactory detection, only volatile flavour molecules, i.e. aroma molecules, can be analysed and detected, while non-volatile flavour molecules such as sugars and salts are not either not extracted or not detected.

The results of the AEDA analysis are tabulated in Table 4 and Table 8 as well as shown in FIG. 2 and FIG. 3.

Example 11. Process to Make Powdered and Paste Flavoured Sweetener and Sweet Sauce Powdered and Paste Flavoured Sweetener Flavoured sweetener was prepared as in Example 2. The flavoured sweetener was transferred into a sealed plastic container for storage at ambient temperature for 2 weeks before being used to prepared powdered and paste flavoured sweetener. To make a powdered sweetener 10 g of flavoured sweetener was heated to approximately 100° C. and mixed with 3.7 g of all-purpose flour (Prima, Singapore) and stirred vigorously by hand. The mixture was dried at 45° C. in an oven overnight, then ground with pestle and mortar to create a dry powder flavoured sweetener.

Alternatively, for a paste flavoured sweetener 10 g of flavoured sweetener was heated to approximately 100° C. and mixed with 1.3 g of all-purpose flour (Prima, Singapore) and stirred vigorously by hand. The resultant mixture was poured into a small mould to create a stock cube or lozenge. When cooled the ambient temperature the paste flavoured sweetener can also be shaped by hand.

Powdered and Paste Sweet Sauce

Sweet sauce was prepared was made from the flavoured sweetener as in Example 8. The flavoured sweetener was transferred into a glass container for storage at ambient temperature for 2 weeks before being used to prepare powdered and paste sweet sauce. To make a powdered sweet sauce 10 g of sweet sauce was mixed with 20 g of all-purpose flour (Prima, Singapore), and stirred vigorously by hand. The mixture was dried at 45° C. in an oven overnight, then ground with pestle and mortar, and dried at 45° C. for three days to create a dry powder.

Alternatively, for a paste sweet sauce, 10 g vegetable oil (Harmuni, Thailand) was mixed with 40 g of all-purpose flour (Prima, Singapore) and stir fried for 5 minutes. 35 g of sweet sauce added and heated to approximately 100° C. and stirred vigorously and the resultant mixture was poured into a small mould to create a stock cube or lozenge.

Example 12. Process to Make Food and Beverage Products with Flavoured Sweeteners Chocolate Bar A chocolate product using flavoured sweetener was prepared by blending 26 g of melted butter in 20 g cocoa powder and 20 g flavoured sweetener until well mixed. The mixture was formed into chocolate moulds and refrigerated.

Hazelnut Spread 60 g unsalted butter was added to 225 g of melted semi-sweet chocolate (70% cocoa) and blended. 100 mL heavy cream was then mixed into the chocolate-butter mix and a pinch of salt added. Meanwhile 140 g of hazelnuts were roasted for 180° C. for 10 minutes and cooled to room temperature before being added to a food processor together with 40 g flavoured sweetener and blended into a smooth paste. Lastly, the chocolate-butter-cream mix was slowly added to the hazelnut-CNS paste, forming a hazelnut spread product.

Pudding

A smooth paste was made using 37 g of custard powder and flavoured sweetener using 2 to 3 tablespoons of milk. Meanwhile, the milk was boiled and added to the paste while boiling and cooked until the custard solution thickened. Lastly, the solution was poured into a mould and either served directly, cooled down or refrigerated.

Almond Energy Bar

The oven was preheated to 180° C. In a large bowl ½ cups oats, ⅛ cups almonds, ⅛ cups cashews or peanuts, ⅛ cups sesame seeds, ⅛ cups sunflower seeds, and ⅛ cups raisins were combined. ⅜ cups tahini and ¼ cups flavoured sweetener were combined in a bowl, and heated in the microwave for 30 seconds. ¼ tsp vanilla extract was added and mixed well. The oat mixture was added to the mixture and stirred until well combined. The mixture was poured out onto a baking sheet and with wet hands formed into a rectangle about 1-inch high. Baked for 15 minutes, until the edges of the bar turned golden brown.

Ginger Tea

A flavoured sweetener was prepared as in Example 1, but the process flow was changed when the temperature reached 115° C. At this point approximately 2 g of fresh finely chopped ginger was added and the mixture stirred vigorously. After a few minutes of further cooking the hot mixture was poured into cubic mould. The total mass of ginger tea cube is approximately 50 g. The ginger tea cube was dissolved in approximately 500 mL of boiling water to produce a sweet ginger tea beverage.

Example 13. Process to Make Food Products with Sweet Sauce Made with Flavoured Sweetener Tempeh and Green Beans Using Spicy Sweet Sauce Made Using the Flavoured Sweetener.

Spicy sweet sauce made using the flavoured sweetener was prepared by adding 1.4 g of chopped bird's eye chili and 3.8 g of chopped garlic to a sweet sauce made with flavoured sweetener produced as in Example 8 together with the soy sauce.

Cooking oil was heated to about 150° C. in a wok or deep fryer. About 200 g of fresh tempeh was added to the hot cooking oil and fried for 10 to 20 minutes until golden brown. The tempeh was cooled down and cut into bite-sized pieces. About 50 g of green beans were washed and boiled in a pot of water with a drop of cooking oil for 5 to 10 minutes. A pan was pre-heated with cooking oil and tempeh was added and stir fried for 3 to 5 minutes. The boiled green beans and chopped chillies were added to the pan and stir fried for an additional 10 minutes. A little salt and 36 g of spicy sweet sauce made with flavoured sweetener was stirred into the pan until covering the stir fried ingredients.

Air-Fried Sweet Corn with Onion Sweet Sauce Made with Flavoured Sweetener

Onion sweet sauce made with flavoured sweetener was prepared by frying 49 g of chopped red onion and 17.7 g of chopped garlic in 69 g of 150° C. cooking oil until golden brown. 2.8 g of red onion and garlic residue in oil was added to a sweet sauce made with flavoured sweetener produced as in Example 8 together with the soy sauce.

An ear of maize was shucked and the sweet corn cob cut into a few pieces. The cob pieces were wrapped in aluminium foil with 16 g of onion sweet sauce made with flavoured sweetener. The aluminium packages were fried in an air fryer (Phillips, The Netherlands) for 25 minutes.

Chicken Stew Using Powdered Sweet Sauce Made with Flavoured Sweetener

A chicken was deboned and cut into pieces and boiled with 500 g of water together with two chopped carrots and two chopped potatoes. After 30 minutes 60 g of powdered sweet sauce made with flavoured sweetener was added and the stew boiled for another 8 minutes.

The chicken stew has a nice sweet and salty taste from the gravy made by the powdered sweet sauce made with flavoured sweetener. The thickness of the gravy is in the appropriate range for a stew, and there are no starch lumps.

Example 14. Method to Make Flavoured Sweetener Using Sugar Beet Juice Incubated with *Bacillus subtilis* and *Bacillus flexus*

Raw Material

The unrefined plant extract containing sucrose as the main solute was a sugar beet juice. The sugar beet juice was obtained from thinly slicing 1 kg sugar beet from China and boiling it for 30 minutes in 1 kg of water. A sugar beet juice with a refractory dry substance (RDS) content of around 10° Bx was obtained. 1 kg of this unrefined plant extracts containing sucrose as the main solute was coarsely filtered with a muslin cloth such as fabrique.

1 kg each of the raw materials was transferred under sterile conditions, using a horizontal laminar flow hood, into a sterile glass bioreactor with an inner diameter of 100 mm and maximum working volume of 1.2 L and equipped with two 46 mm diameter 6-blade Rushton impellers and a L-sparger, pH sensor (Mettler Toledo, Switzerland), an optical dissolved oxygen (DO) sensor (Hamilton, U.S.A.). The bioreactor was inserted into a DASGIP multi-incubator (Eppendorf, Germany) 'bioblock', which is a metal block with heating and cooling functions, to adjust the temperature of the bioreactor contents to 33° C.

A two-point pH calibration was carried out using pH 4 and 7 buffers, and DO calibration was performed while gassing the bioreactor at a rate of 0.1 vvm while agitating the bioreactor at 400 rpm until the DO sensor value had stabilised at 100%.

Inoculum

Individual overnight cultures of strains *Bacillus subtilis* and *Bacillus flexus* from cryo-preserved strain collection were prepared in 30 mL sterile CMO 129 tryptic soy broth (TSB) (Oxoid, U.K.) in a 50 mL conical test tube, incubated at 33° C. and shaken at 250 rpm for approximately 20 hrs.

The concentration of cells in the inoculum was evaluated through the optical density (OD). 1 mL of bacterial suspension was transferred into a 1.5 mL conical micro test tube and centrifuged on a centrifuge model 5810 with rotor A-4-62 (Eppendorf, Germany) for 5 min at 3220 relative centrifugal force (RCF).

The supernatant was decanted, re-suspended with 1 mL de-ionised (DI) water, transferred to disposable cuvette and measure OD at 600 nm in an 1634-6041 double-beam spectrophotometer UV-6300PC (VWR, U.S.) blanked with DI water.

Incubation pH was adjusted prior to and during the incubation and remained within 5.8 to 6.2 throughout the incubation. Incubation was initiated by the addition into the bioreactor of a 0.5% by volume inoculum scaled by the inverse of the measured OD at 600 nm of each inoculum: i.e. OD=1 gives an inoculation volume of 5 mL, while OD=0.5 gives an inoculation volume of 10 mL. DO was controlled during the incubation by an oxygen cascade. The oxygen cascade provides a minimum of 400 rpm agitation and 0.1 vvm gassing. The oxygen cascade will keep the DO at a minimum of 30% by sequentially increasing agitation up to 1200 rpm and gassing up to 0.3 vvm.

Cooking

The modified unrefined plant extracts containing sucrose as the main solute was transferred to a stainless steel bowl and brought to boil on an electric hotplate (Heidolph, Germany) with temperature control. Initially the temperature set point was 200° C. on the hotplate, until the modified unrefined plant extract started boiling at a process temperature of 100° C., and the set point was reduced to 150° C. When the process temperature reached 105° C., then the temperature set point was further reduced to 120° C. From this point the viscous syrup was stirred continuously by hand to avoid overheating and burning. Development of a brown, slightly metallic, caramel-like aroma and dark red brown colour development was detected. When the process temperature reached approximately 120° C. the bowl was taken off the hotplate and stirred vigorously for 3 minutes. During these 3 minutes the syrup became more viscous, and then grew lighter in colour and opaque, until becoming a solid semi-crystalline product.

The invention claimed is:

1. A process for making a coconut sugar substitute comprising:
   a. pasteurizing an unrefined sucrose-based plant extract containing sucrose as the main solute by heating, wherein the unrefined sucrose-based plant extract is selected from the group consisting of sugarcane juices, jaggeries, sugarcane juices mixed with sugarcane molasses, and sugarcane syrups;
   b. fermenting the pasteurized unrefined sucrose-based plant extract under aerobic conditions with at least one aerobic microbial strain to form a modified unrefined sucrose-based plant extract wherein the at least one aerobic microbial strain is an osmo-tolerant and/or a halo-tolerant aerobic microbial strain capable of growing in a medium with a refractometric dry substance content of 8° Bx to 40° Bx, and wherein the at least one aerobic microbial strain is selected from *Stenotrophomonas maltophilia*, *Bacillus flexus*, *Bacillus subtilis*, and *Kluyveromyces* species;
   c. evaporating water from the modified sucrose-based plant extract to form a concentrate; and
   d. cooking the concentrate to develop colour and flavour to produce the coconut sugar substitute,
wherein the modified unrefined sucrose-based plant extract is heated and cooked until reaching a temperature and refractometric dry substances content of 65° C. to 170° C. and 50° Bx to 100° Bx.

2. A coconut sugar substitute produced by the process according to claim 1.

3. A process of making a flavour extract comprising:
   (a) making a coconut sugar substitute according to the process of claim 1, and
   (b) isolating one or more aroma chemical molecules from the modified sucrose-based plant extract, or the coconut sugar substitute, or a syrup of the coconut sugar substitute, or a crystal phase of the coconut sugar substitute.

4. A process for manufacturing a food product, comprising:
   a. making a coconut sugar substitute according to the process of claim 1;
   b. mixing the coconut sugar substitute with an additional ingredient; and
   c. forming the food product.

5. A process for manufacturing a food product, comprising:
   a. making a flavour extract according to the process of claim 3;
   b. mixing the flavour extract with an additional ingredient; and
   c. forming the food product.

6. A food product produced by the process of claim 4.

7. The process of claim 1, further comprising the step of adjusting the unrefined sucrose-based plant extract to a refractometric dry substance content of 8° Bx to 40° Bx prior to the fermentation step (b).

8. The process of claim 1, further comprising the step of adjusting the unrefined sucrose-based plant extract to a refractometric dry substance content of 10° Bx to 35° Bx prior to the fermentation step (b).

9. The process of claim 1, further comprising heating the modified unrefined sucrose-based plant extract of step (b) until reaching a temperature of 65° C. to 170° C. prior to the evaporating step (c).

10. The process of claim 1, wherein fermenting the unrefined sucrose-based plant extract in step (b) is performed for 3 hours to 5 hours, at a temperature of about 33° C., at a pH around 6, and a relative dissolved oxygen concentration of at least 20%.

11. The process of claim 1, wherein pasteurizing the unrefined sucrose-based plant extract in step (a) is performed at a temperature of 70° C. to 72° C. for about 2 minutes.

12. The process of claim 1, wherein the modified unrefined sucrose-based plant extract is heated and cooked until reaching a temperature and refractometric dry substances content of 110° C. to 130° C. and 75° Bx to 95° Bx.

13. The process of claim 1, wherein the modified unrefined sucrose-based plant extract is heated and cooked until reaching a temperature and refractometric dry substances content of 120° C. and 90° Bx.

* * * * *